(12) United States Patent
Segal et al.

(10) Patent No.: US 7,211,250 B2
(45) Date of Patent: May 1, 2007

(54) METHOD AND COMPOSITION FOR INHIBITING CANCER CELL GROWTH

(75) Inventors: Don Segal, Stouffville (CA); Jerry McElroy, Richmond Hill (CA); Heman Chao, Aurora (CA); Wah Wong, Edmonton (CA); John Docherty, Aurora (CA); Jodi Dickstein, Markham (CA)

(73) Assignee: Helix Biopharma Corporation, Aurora, Ontario (CA)

( * ) Notice: Subject to any disclaimer, the term of this patent is extended or adjusted under 35 U.S.C. 154(b) by 351 days.

(21) Appl. No.: 10/621,833

(22) Filed: Jul. 16, 2003

(65) Prior Publication Data

US 2004/0115186 A1 Jun. 17, 2004

Related U.S. Application Data

(60) Provisional application No. 60/397,244, filed on Jul. 18, 2002.

(51) Int. Cl.
*A61K 38/46* (2006.01)
*C12N 9/78* (2006.01)
*C12Q 1/58* (2006.01)

(52) U.S. Cl. .................. 424/94.6; 435/12; 435/227

(58) Field of Classification Search .................. None
See application file for complete search history.

(56) References Cited

U.S. PATENT DOCUMENTS

| | | | |
|---|---|---|---|
| 4,837,380 A * | 6/1989 | Deftos et al. | 424/450 |
| 5,411,884 A * | 5/1995 | Hellstrom et al. | 435/344.1 |
| 5,573,934 A * | 11/1996 | Hubbell et al. | 435/177 |
| 5,750,496 A * | 5/1998 | Forney et al. | 514/2 |
| 6,126,938 A | 10/2000 | Guy et al. | |
| 6,248,330 B1 | 6/2001 | Labigne et al. | |
| 6,426,086 B1 * | 7/2002 | Papahadjopoulos et al. | 424/450 |
| 2003/0108966 A1 * | 6/2003 | Mather | 435/7.23 |

FOREIGN PATENT DOCUMENTS

| | | |
|---|---|---|
| WO | WO 95/22987 | 8/1995 |
| WO | WO95/31480 * | 11/1995 |
| WO | WO 98/37207 | 8/1998 |
| WO | WO 01/00245 | 1/2001 |

OTHER PUBLICATIONS

Int'l. Search Report from Int'l. Appln. No. PCT/CA03/01061; Int'l. Filing Date: Jul. 16, 2003.
Bagshawe, K.D., et al., "A cytotoxic agent can be generated selectively at cancer sites," *Br. J. Cancer* 58 pp. 700-703 (1988).
Herron, J.N., et al., "Antibodies and targeting moieties: affinity measurements, conjugation chemistry and applications in immunoliposomes," *J. Controlled Release* 28:1/3 pp. 155-166 (1994).
Raghunand, N., et al., "Enhancement of chemotherapy by manipulation of tumour pH," *B. J. Cancer* 80:7 pp. 1005-1011 (1999).
Shi, G., et al., "Efficient intracellular drug and gene delivery using folate receptor-targeted pH-sensitive liposomes composed of cationic/anionic lipid combinations," *J. Controlled Release* 80:1-3 pp. 309-319 (2002).
Wampler, G.L., et al., "Antitumor activity of acetohydroxamic acid," *Proceedings of AACR and ASCO, Abstract* 18 p. 214 (1977).
Zimber, A., et al., "Effect of Urease Injections on Ehrlich Ascites Tumor Growth in Mice," *Proceedings of the Society for Experimental Biology and Medicine* 139:1 143-149 (1972).

* cited by examiner

*Primary Examiner*—Robert A. Wax
(74) *Attorney, Agent, or Firm*—Perkins Coie LLP; Peter J. Dehlinger

(57) ABSTRACT

A pharmaceutical composition and method for use in inhibiting growth of cancer cells in a mammalian subject are disclosed. The composition includes a urease enzyme, and associated therewith, a chemical entity effective to enhance the delivery of the enzyme to cancer cells, when the composition is administered to the subject. Also disclosed are a method of enhancing the effectiveness of weakly basic anti-tumor compounds, a method assessing the presence, size or condition a solid tumor in a subject, and a gene therapy composition for treating a cancer in a subject.

34 Claims, 5 Drawing Sheets

Affinity Purification of Urease

Affinity Purification of Urease

METHOD AND COMPOSITION FOR INHIBITING CANCER CELL GROWTH

CROSS-REFERENCE TO RELATED APPLICATIONS

This application claims priority to and benefit of U.S. Provisional Patent Application Ser. No. 60/397,244, filed Jul. 18, 2002, the disclosure of which is incorporated herein by reference in its entirety for all purposes.

FIELD OF THE INVENTION

The present invention relates to anticancer therapeutic methods employing urease proteins and polypeptides.

BACKGROUND OF THE INVENTION

Cancer accounts for one-fifth of the total mortality in the United States, and is the second leading cause of death. Cancer is typically characterized by the uncontrolled division of a population of cells. This uncontrolled division may involve blood cells, such as various types of lymphomas, or cells that aggregate in or are native to a particular tissue or organ, e.g., solid tumors, such as secondary or primary tumors of the breast, liver, esophagus, stomach, intestines, brain, bone, or prostate.

A variety of treatment modalities have been proposed for cancer therapy. These generally include surgical resection of solid tumors, treatment with radiation, such as x-ray, chemotherapy, immune therapy, and gene therapy. The type(s) of therapy that are selected for a given cancer will depend on such factors as patient age, degree of localization of the cancer, and the type and stage of the cancer. Often the therapy will involve a combination of two or more modalities, such as x-ray therapy in combination with chemotherapy, or with immunotherapy in combination with chemotherapy.

A large number of chemotherapeutic compounds and compositions and strategies have been employed in treating cancers. Many anti-neoplastic compounds are designed to disrupt replication in rapidly dividing cells, or to inhibit a key metabolic link in actively proliferating cells. Although such approaches have met with levels of success in certain types of cancers, or cancers at certain stages, chemotherapy is generally associated with unpleasant to debilitating side effects, such as malaise, nausea, loss of appetite, alopecia, and anemia. Further, compounds which act at the level of cell replication, either by introducing nucleotide analogs into dividing cells, or by disrupting normal replication, have the potential of introducing widespread genetic mutations in normal cells in the subject. In addition, cancer cells may develop resistance to many types of anti-tumor agents, either by limiting uptake of the agent into the cells, or by altering the metabolism of the agent within the cells.

In response to these limitations, attempts to modify chemotherapeutic agents to reduce their side effects, overcome problems of resistance, or improve their targeting to selected tumor sites have been developed. While these efforts have yielded improved therapeutic results in some cases, there remains a need to provide an improved chemotherapeutic agent and method. In particular, such an agent should be effective in killing or inhibiting the growth of cancer cells, should be relatively non-toxic both in terms of side effects and long-term effects on the genetic integrity of the treated subject, and preferably deliverable in a form that allows direct introduction into a tumor or selective targeting to tumors.

SUMMARY OF THE INVENTION

The invention provides a pharmaceutical composition for use in inhibiting growth of cancer cells in a mammalian subject. The composition includes a urease enzyme, such as bacterial or plant urease, and a chemical entity associated with the urease for enhancing the delivery of the enzyme to cancer cells, when the composition is administered to the subject.

In one embodiment, the chemical entity includes a hydrophilic polymer conjugated to the urease in an amount effective to extend the blood circulation time or reduce the antigenicity of said composition relative to native urease. The polymer may be, for example, polyethylene glycol, polyvinylpyrrolidone, polyvinylmethylether, polyhydroxypropyl methacrylamide, polyhydroxypropyl methacrylate, polyhydroxyethyl acrylate, polymethacrylamide, polydimethylacrylamide, polymethyloxazoline, polyethyloxazoline, polyhydroxyethyloxazolione, polyhydroxypropyoxazoline, polyaspartamide, or hydrophilic cellulose derivatives. The polymer is preferably a linear chain polymer, such as polyethylene glycol linear chain, having a molecular weight between about 1,000 and 10,000 daltons.

The chemical entity may be a targeting moiety attached to the urease, such as an anti-tumor antigen antibody, anti-hCG antibody, or a ligand capable of binding specifically to cancer-cell surface receptors. Where the targeting moiety is a polypeptide, the composition may be a fusion protein of the targeting moiety and urease enzyme. Alternatively, where the urease may include, at its C- or N-terminus, a first coil-forming peptide characterized by a selected charge and an ability to interact with a second, oppositely charged coil-forming peptide to form a stable α-helical coiled-coil heterodimer; and the chemical entity may include a targeting moiety which includes the second coil-forming peptide.

The chemical entity may include vesicles having urease enzyme in entrapped form. Exemplary vesicles include liposomes, which are long-circulating by virtue of an exterior coating of polyethylene glycol chains and sized to extravasate into tumor regions, when the composition is administered intravenously, and liposomes having surface bound targeting moieties. The vesicles may include additional agents, such as urea, a therapeutically active anti-tumor agent or an imaging agent.

The chemical entity may include a urease inhibitor associated therewith, in an amount sufficient to inhibit the activity of said enzyme.

In another aspect, the invention includes a method for inhibiting growth of cancer cells in a mammalian subject. The method includes exposing the cells to urease in an amount effective to inhibit growth of the cancer cells.

Where the cancer cells comprise a solid tumor, the urease may be injected directly into the tumor of the subject, or by parenteral administration, e.g., injection, other than by direct administration. In addition to urease in a pharmaceutically acceptable carrier, the various compositions containing urease noted above are suitable for use in the invention.

The method may include modulating the activity of urease on cancer cells by administering to the subject, an amount of a urease inhibitor effective to reduce the activity of urease on said cancer cells. Urease activity may be modulated in the opposite direction by administering urea to the subject, before, during, or after urease administration.

The urease may be administered in two stages: a first stage involving a conjugate of a tumor targeting moiety and a first binding moiety having an ability to interact with a second binding moiety; and a second stage second conjugate comprising the second binding moiety conjugated with urease.

In still another embodiment, the method may include administering to the subject, a gene therapy composition composed of a targeting vector effective, when administered to the subject, of selectively transfecting cancer cells, and carried in said vector, a recombinant nucleic acid sequence effective to produce a urease mRNA in transfected cancer cells. An exemplary vector is an adenovirus. An exemplary nucleic acid sequence encodes urease and a secretory leader sequence effective to promote secretion of the urease from the transfected cancer cells.

In a related aspect, the invention provides a method of enhancing the therapeutic efficacy of a weakly basic anti-tumor compound whose effectiveness is reduced by a higher intracellular/lower extracellular pH gradient in a solid tumor, in a subject receiving the agent for tumor treatment. This method involves administering to the subject, an amount of urease effective to reduce or reverse the higher intracellular/lower extracellular pH gradient in a solid tumor. Preferably, the amount of urease administered is effective to raise the extracellular fluid of the tumor to at least pH 7.2. The urease may be injected directly into the tumor, or by parenteral administration other than direct administration, as above.

The anti-tumor compound may be, for example, doxorubicin, daunorubicin, mitoxanthrone, epirubicin, mitomycin, bleomycin, vinca alkaloids, such as vinblastine and vincristine, alkylating agents, such as cyclophosphamide and mechlorethamine hydrochloride, and antrineoplastic purine or pyrimidine derivatives.

In still another aspect, the invention is useful in assessing the presence, size or condition of a solid tumor in a subject. Here, urease is administered to the subject containing, or suspected of containing, a solid tumor, under conditions effective to localize the urease in a solid tumor in the subject. The subject is then interrogated with a diagnostic tool, such as fluoroscopy, MRI, or positron emission tomography, capable of detecting changes in extracellular pH in a subject's tissue, in either the presence or absence of a pH-sensitive reporter, for identifying a tissue region within the subject that shows an elevation in extracellular pH.

This method may be used in conjunction with the above treatment method to assess the extent and/or effectiveness of urease dosing or treatment. Thus, for example, in administering urease to a subject, the extent and degree of pH change in a tumor region can be followed to guide urease administration, or to assess changes in tumor size or extent during treatment.

Also disclosed is a kit for use in inhibiting growth of cancer cells in a mammalian subject. The kit has a pharmaceutical composition containing urease enzyme, and instructional materials teaching the administration of the composition to a subject, for the treatment of a cancer in the subject.

The instructional material may teach administering the urease composition to a subject in an amount which is dependent on the size of the tumor and between 0.1 to 100 international units, preferably 0.5 to 10, urease activity per $mm^3$ tumor, when the composition is administered by direct injection into the tumor, and in an amount between 100–100,000 international units/kg, preferably 500–10,000 international units/kg international units urease activity/kg subject body weight, when the composition is administered parenterally to the subject other than by direct injection into the tumor.

The instruction material may teach administering urease to a subject who is also receiving a weakly basic anti-tumor compound whose effectiveness is reduced by a higher intracellular/lower extracellular pH gradient in a solid tumor, in an amount of urease effective to reduce or reverse the higher intracellular/lower extracellular pH gradient in a solid tumor.

The instruction material may teach administering urease to a subject containing, or suspected of containing, a solid tumor, under conditions effective to localize the urease in a solid tumor in the subject, interrogating the subject with a diagnostic tool capable of detecting changes in extracellular pH in a subject's tissue, and identifying a tissue region within the subject that shows an elevation in extracellular pH following said administering.

Also disclosed is a gene therapy composition for use in inhibiting growth of cancer cells in a mammalian subject. This composition includes, as noted above, a targeting vector effective, when administered to the subject, of selectively transfecting cancer cells, and carried in the vector, a recombinant nucleic acid sequence effective to produce a urease mRNA in transfected cancer cells.

These and other objects and features of the invention will become more fully apparent when the following detailed description of the invention is read in conjunction with the accompanying drawings.

DETAILED DESCRIPTION OF THE INVENTION

I. Definitions

Figure 1A:
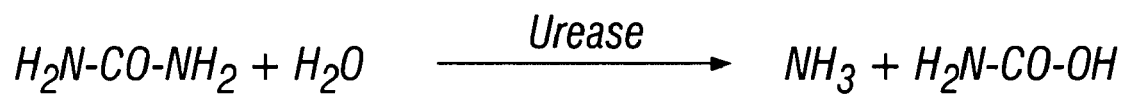
FIGS. 1A–1D illustrate the steps of the urease reaction. Urea is cleaved by urease to produce one molecule of ammonia and one of carbamate (A). Carbamate spontaneously decomposes to ammonia and carbonic acid (B). The carbonic acid equilibrates in water (C), as do the two molecules of ammonia, which become protonated to yield ammonium and hydroxide ions (D). The reaction results in a rise in the pH of the reaction environment.
Figure 1B:
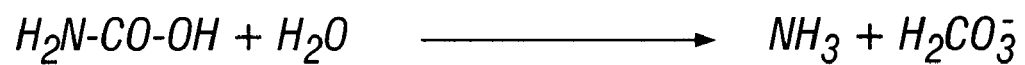
Figure 1C:
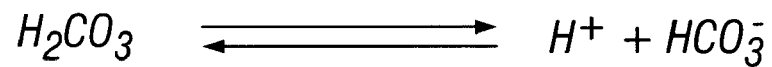
Figure 1D:

Unless otherwise indicated, all technical and scientific terms used herein have the same meaning as they would to one skilled in the art of the present invention. Practitioners are particularly directed to Sambrook et al. (2001) "Molecular Cloning: A Laboratory Manual" Cold Spring Harbor Press, 3rd Ed.; and Ausubel, F. M., et al. (1993) in Current Protocols in Molecular Biology, for definitions and terms of the art. It is to be understood that this invention is not limited to the particular methodology, protocols, and reagents described, as these may vary.

The term "urease" refers to an enzyme having the enzymatic activity of a urea amidohydrolase (E.C. 3.5.1.5), either naturally occurring or obtained by e.g., recombinant nucleic acid techniques and/or chemical synthesis. Urease also includes fusion proteins comprising the entire urease, subunits, or fragments thereof, and/or urease with amino acid substitutions, deletions or additions that preserve the urea amidohydrolase activity of the polypeptide. A truncated urease sequence as used herein is a fragment of urease that is free from a portion of the intact urease sequence beginning at either the amino or carboxy terminus of urease. Methods for isolating native urease, for synthesizing urease recombinantly, and for identifying active fragments and modified urease polypeptides are given below.

The term "cancer" is meant to refer to an abnormal cell or cells, or a mass of tissue. The growth of these cells or tissues exceeds and is uncoordinated with that of the normal tissues or cells, and persists in the same excessive manner after cessation of the stimuli which evoked the change. These neoplastic tissues or cells show a lack of structural organization and coordination relative to normal tissues or cells which may result in a mass of tissues or cells which can be either benign or malignant. As used herein, cancer includes any neoplasm. This includes, but is not limited to, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, and the like.

A "tumor" or "solid tumor" refers to a cohesive mass of cancer cells, including but not limited to semi-solid and solid tumors, solid tumor metastases, angiofibromas, retrolental fibroplasia, hemangiomas, and Karposi's sarcoma.

As used herein, the term "targeting moiety" refers to a molecule that binds to a defined population of cells or selected cell type. The targeting moiety may bind a receptor, an oligonucleotide, an enzymatic substrate, an antigenic determinant, or other binding site present on or in the target cell or cell population. An exemplary targeting moiety is an antibody. Antibody fragments and small peptide sequences capable of recognizing expressed antigens are also contemplated targeting moieties.

As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

As used herein, the term "induces apoptosis" refers to the promotion of a form of programmed cell death characterized by DNA fragmentation. Apoptosis can be determined by methods known in the art. For example, kits are commercially available that detect the presence of fragmented DNA by in situ immunohistochemistry (e.g., Apoptag, available from Intergen, Purchase, N.Y.). Additionally, apoptosis can also be determined by FACS analysis, in which apoptotic cells exhibit a sub-G1 DNA content, indicating DNA fragmentation.

As used herein, an "antibody" refers to a peptide, polypeptide, or protein comprising one or more peptides or polypeptides substantially or partially encoded by at least one immunoglobulin nucleic acid molecule or immunoglobulin gene or fragment of at least one immunoglobulin molecule or immunoglobulin gene. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" chain (about 25 kD) and one "heavy" chain (about 50–70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively. Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the (Fab')2 dimer into an Fab' monomer. The Fab' monomer is essentially a Fab with part of the hinge region (see *Fundamental Immunology*, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term "antibody", as used herein, also includes antibody fragments either produced by the modification of whole antibodies or synthesized de novo using recombinant DNA methodologies. Antibodies include single chain antibodies, including single chain Fv (sFv) antibodies in which a VH and a VL are joined together (directly or through a peptide linker) to form a continuous polypeptide.

An "antigen-binding fragment" of an antibody is a peptide or polypeptide fragment of the antibody that binds an antigen. An antigen-binding site is formed by those amino acids of the antibody that contribute to, are involved in, or affect the binding of the antigen. See Scott, T. A. and Mercer, E. I., CONCISE ENCYCLOPEDIA: BIOCHEMISTRY AND MOLECULAR BIOLOGY (de Gruyter, 3d ed. 1997)

and Watson, J. D. et al., RECOMBINANT DNA (2d ed. 1992), each of which is incorporated herein by reference in its entirety for all purposes. The term "antibody fragment" also includes any synthetic or genetically engineered protein that acts like an antibody by binding to a specific antigen to form a complex.

The terms "active agent", "drug" and "pharmacologically active agent" are used interchangeably herein to refer to a chemical material or compound which, when administered to a subject induces a desired pharmacologic effect, and is intended to include a diagnostic or therapeutic agent, including radionuclides, drugs, anti-cancer agents, toxins and the like. Preferably, the term active agent includes proteins, glycoproteins, natural and synthetic peptides, alkaloids, polysaccharides, nucleic acid molecules, small molecules and the like. More preferably, the term active agent refers to proteins. An exemplary active agent is urease.

A "pH-sensitive" active agent refers to an active agent whose ability to induce a desired pharmacologic effect depends, at least in part, on the pH of the surrounding extracellular environment.

The term "clearing agent", as used herein, refers to an agent capable of binding, complexing or otherwise associating with an administered moiety, e.g., targeting moiety-ligand, targeting moiety-anti-ligand or anti-ligand alone, present in the recipient's circulation, thereby facilitating circulating moiety clearance from the recipient's body, removal from blood circulation, or inactivation thereof in circulation. The clearing agent is preferably characterized by physical properties, such as size, charge, configuration or a combination thereof, that limit clearing agent access to the population of target cells recognized by a targeting moiety used in the same treatment protocol as the clearing agent.

The term "imaging agent" is meant to refer to compounds which can be detected.

The term "adjuvant" refers to a substance or agent added to a formulation or composition to aid the operation of the main ingredient.

The terms "interstitial" and "extracellular" fluid refer to the fluid lying between or bathing the cells of mammals.

The terms "subject", "individual" and "patient" are used interchangeably herein to refer to any target of the treatment. Also provided by the present invention is a method of treating tumor cells in situ, or in their normal position or location, for example, neoplastic cells of breast or prostate tumors. These in situ tumors can be located within or on a wide variety of hosts; for example, human hosts, canine hosts, feline hosts, equine hosts, bovine hosts, porcine hosts, and the like. Any host in which is found a tumor or tumor cells can be treated and is in accordance with the present invention. A subject thus includes a vertebrate, preferably a mammal, more preferably a human.

By "target cell retention time" is intended the amount of time that a urease molecule or other active agent remains at the target cell surface or within the target cell.

As used herein, the term "conjugate" encompasses chemical conjugates (covalently or non-covalently bound), fusion proteins and the like.

The terms "protein", "polypeptide" or "peptide", as used herein, refer interchangeably to a biopolymer composed of amino acid or amino acid analog subunits, typically some or all of the 20 common L-amino acids found in biological proteins, linked by peptide intersubunit linkages, or other intersubunit linkages. The protein has a primary structure represented by its subunit sequence, and may have secondary helical or pleat structures, as well as overall three-dimensional structure. Although "protein" commonly refers to a relatively large polypeptide, e.g., containing 100 or more amino acids, and "peptide" to smaller polypeptides, the terms are used interchangeably herein. That is, the term "protein" may refer to a larger polypeptide, as well as to a smaller peptide, and vice versa.

A "modulator of urease" is either an inhibitor of urease or an enhancer of urease.

An "inhibitor of urease" comprises a molecule or group of molecules that interferes with: (1) the expression, modification, regulation, activation or degradation of urease; or (2) one or more of the normal functions of urease. The normal functions of urease include the hydrolysis of urea, leading to the production of carbamate and ammonia. An inhibitor "acts directly on urease" when the inhibitor binds to urease via electrostatic or chemical interactions. Such interactions may or may not be mediated by other molecules. An inhibitor acts "indirectly on urease" when its most immediate effect is on a molecule other than urease which influences the expression, activation or functioning of urease.

An "enhancer of urease" comprises a molecule or group of molecules that enhances: (1) the expression, modification, regulation or activation of urease; or (2) one or more of the normal functions of urease. An enhancer acts "indirectly on urease" when its most immediate effect is on a molecule other than urease which influences the expression, activation or functioning of urease.

An "engineered mutation" in a urease gene comprises a change in nucleotide sequence of the urease gene that results in the production of (1) increased or reduced amounts of urease protein relative to the amounts produced in the absence of such change; or (2) urease protein having enhanced or impaired normal functions relative to such functions in the absence of such changes.

The term "pharmaceutical composition" means a composition suitable for pharmaceutical use in a subject, including an animal or human. A pharmaceutical composition generally comprises an effective amount of an active agent and a carrier, including, e.g., a pharmaceutically acceptable carrier.

A "pharmaceutically acceptable formulation" comprises a formulation that is suitable for administering the active agent (e.g., urease or urease modulator) in a manner that gives the desired results and does not also produce adverse side effects sufficient to convince a physician that the potential harm to a patient is greater than the potential benefit to that patient. The basic ingredient for an injectable formulation is typically a water vehicle. Aqueous vehicles that are useful include sodium chloride (NaCl) solution, Ringer's solution, NaCl/dextrose solution, and the like. Water-miscible vehicles are also useful to effect full solubility of the active agent. Antimicrobial agents, buffers and antioxidants may be useful, depending on the need. Similarly, a "pharmaceutically acceptable" salt or a "pharmaceutically acceptable" derivative of a compound, as provided herein, is a salt or other derivative which is not biologically or otherwise undesirable.

The term "controlled release" is intended to refer to any drug-containing formulation in which the manner and profile of drug release from the formulation are controlled. The term "controlled release" refers to immediate as well as non-immediate release formulations, with non-immediate release formulations including but not limited to sustained release and delayed release formulations.

The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release."

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such as a nucleic acid, vector, gene, polypeptide, protein, substance, or composition thereof, that eliminates or diminishes signs or symptoms of pathology, disease or disorder, when administered to a subject suffering from such signs or symptoms. A "therapeutically useful" agent or compound (e.g., nucleic acid or polypeptide) indicates that an agent or compound is useful in diminishing, treating, or eliminating such signs or symptoms of a pathology, disease or disorder.

The term "small molecule" includes a compound or molecular complex, either synthetic, naturally derived, or partially synthetic, and which preferably has a molecular weight of less than 5,000 Daltons. More preferably, a small molecule has a molecular weight of between 100 and 1,500 Daltons.

The terms "nucleic acid molecule" or "oligonucleotide" or grammatical equivalents herein, refer to at least two nucleotides covalently linked together, and typically refers to RNA, DNA and cDNA molecules. A nucleic acid of the present invention is preferably single-stranded or double-stranded, and will generally contain phosphodiester bonds, although in some cases nucleic acid analogs are included that may have alternate backbones comprising, for example, phosphoramide, phosphorothioate, phosphorodithioate, and/or O-methylphosphoroamidite linkages. It will be understood that, as a result of the degeneracy of the genetic code, a multitude of nucleotide sequences encoding given peptides such as urease may be produced.

A "heterologous" nucleic acid construct or sequence has a portion of the sequence which is not native to the cell in which it is expressed. Heterologous, with respect to a control sequence, refers to a control sequence (i.e., promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A heterologous nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, an "expression cassette" or "expression vector" is a nucleic acid construct generated recombinantly or synthetically, with a series of specified nucleic acid elements that permit transcription of a particular nucleic acid in a target cell or in vitro. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in host cells and where expression of the selectable marker confers to cells containing the expressed gene the ability to grow in the presence of a corresponding selective agent.

As used herein, the terms "promoter" and "transcription initiator" refer to a nucleic acid sequence that functions to direct transcription of a downstream gene. The promoter will generally be appropriate to the host cell in which the target gene is being expressed. The promoter, together with other transcriptional and translational regulatory nucleic acid sequences (also termed "control sequences"), are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed host cells. A typical chimeric gene of the present invention, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "gene" means the segment of DNA involved in producing a polypeptide chain, that may or may not include regions preceding and following the coding region, e.g., 5' untranslated (5' UTR) or "leader" sequences and 3' UTR or "trailer" sequences, as well as intervening sequences (introns) between individual coding segments (exons).

As used herein, "recombinant" includes reference to a cell or vector that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

The term "introduced", in the context of inserting a nucleic acid sequence into a cell, means "transfection", "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, the term "expression" refers to the process by which a polypeptide is produced based on the nucleic acid sequence of a gene. The process includes both transcription and translation.

The term "signal sequence" refers to a sequence of amino acids at the N-terminal portion of a protein which facilitates the secretion of the mature form of the protein outside the cell. The mature form of the extracellular protein lacks the signal sequence which is cleaved off during the secretion process.

By the term "host cell" is meant a cell that contains a vector and supports the replication, or transcription and translation (expression) of the expression construct. Host cells for use in the present invention can be prokaryotic cells, such as E. coli, or eukaryotic cells such as yeast, plant, insect, amphibian, or mammalian cells.

As used herein, "effective amount" or "pharmaceutically effective amount" of an active agent refers to an amount sufficient to derive a measurable change in a physiological parameter of the target cell or subject and/or to provide or modulate active agent expression or activity through administration of one or more of the pharmaceutical dosage units. Such effective amount may vary from person to person depending on their condition, height, weight, age, and/or health, the mode of administering the active agent (e.g., urease or urease modulator), the particular active agent administered, and other factors. As a result, it may be useful to empirically determine an effective amount for a particular patient under a particular set of circumstances.

All publications and patents cited herein are expressly incorporated herein by reference for the purpose of describing and disclosing compositions and methodologies which might be used in connection with the invention.

II. Composition of the Invention

The invention includes, in one aspect, a composition containing urease as an active agent for use in inhibiting growth of cancer cells. A chemical entity may be associated with the active agent, as described below, to enhance the delivery of the active agent to cancer cells. It has been discovered that exposing cancer cells in a patient to urease, as described herein, provides an effective treatment for cancer in the patent. The cancer cells may be contained within a tumor, e.g., a solid or semi-solid tumor. Alternatively, the cancer cells may be circulating in the bloodstream of a subject.

Cancers, tumors and/or neoplasms include new growths of cells or tissue in which the multiplication of cells is uncontrolled and progressive. Some such growths are benign, but others are termed "malignant," leading to death of the organism. Malignant neoplasms are distinguished from benign growths in that, in addition to exhibiting aggressive cellular proliferation, cancers invade surrounding tissues and metastasize. Moreover, malignant neoplasms are characterized in that they show a greater loss of differentiation, and of their organization relative to one another and their surrounding tissues.

Considered below are the components included in the compositions of the invention.

A. Urease

As noted above, the active agent in the composition is urease. The urease may be of any origin, including, e.g., bacteria, plants, fungi and viruses. A number of studies have provided detailed information about the genetics of ureases from a variety of evolutionarily diverse bacteria, plants, fungi and viruses (Mobley, H. L. T. et al. (1995) *Microbiol. Rev.* 59: 451–480; Eur. J. Biochem., 175, 151–165 (1988); Labigne, A. (1990) International publication No. WO 90/04030; Clayton, C. L. et al. (1990) *Nucleic Acid Res.* 18, 362; and U.S. Pat. Nos. 6,248,330 and 5,298,399, each of which is incorporated herein by reference). Of particular interest is urease that is found in plants (Sirko, A. and Brodzik, R. (2000) *Acta Biochim Pol* 47(4):1189–95). One exemplary plant urease is jack bean urease, which is described in Examples 2–3. An exemplary amino acid sequence of jack bean urease is represented by SEQ ID NO: 7.

Useful urease sequences may be identified in public databases, e.g., Entrez (www.ncbi.nlm.nih.gov/Entrez/). Additionally, primers that are useful for amplifying ureases from a wide variety of organisms may be utilized by employing the CODEHOP (COnsensus-DEgenerate Hybrid Oligonucleotide Primer) as described in Rose, et al. (1998) *Nucl. Acids Res.* 26:1628.

The urease may contact the tumor cells, be positioned in the extracellular environment or interstitial fluid surrounding the tumor cells, or be expressed within the cancer cells or cells nearby the cancer cells. While not wishing to be bound by any specific molecular mechanisms underlying the successful inhibition of growth of cancer cells by urease, the urease compound may raise the pH of interstitial fluid in which the cancer cells are bathed, by addition of urease to the interstitial fluid in the subject. Urease can convert the substrate urea to ammonia and carbamate. This enzymatic activity may increase the pH making the environment more basic (FIGS. 1A–1D). The environment around a cancer cell is typically acidic (Webb, S. D., et al. (2001) *Novartis Found Symp* 240:169–81. Thus, by raising the pH of the extracellular environment in this manner, growth of the cancer cell is inhibited. Accordingly, addition of the active agent in certain embodiments of the invention causes the pH of the interstitial fluid to be raised by about 0.1 pH unit, e.g., 0.1–0.5 pH units or greater.

Thus, active agents of the invention include the naturally occurring forms of urease as well as functionally active variants thereof. Two general types of amino acid sequence variants are contemplated. Amino acid sequence variants are those having one or more substitutions in specific amino acids which do not destroy the urease activity. These variants include silent variants and conservatively modified variants which are substantially homologous and functionally equivalent to the native protein. A variant of a native protein is "substantially homologous" to the native protein when at least about 80%, more preferably at least about 90%, even more preferably at least about 95%, yet even more preferably 98%, and most preferably at least about 99% of its amino acid sequence is identical to the amino acid sequence of the native protein. A variant may differ by as few as 1 or up to 10 or more amino acids.

A second type of variant includes size variants of urease which are isolated active fragments of urease. Size variants may be formed by, e.g., fragmenting urease, by chemical modification, by proteolytic enzyme digestion, or by combinations thereof. Additionally, genetic engineering techniques, as well as methods of synthesizing polypeptides directly from amino acid residues, can be employed to produce size variants.

By "functionally equivalent" is intended that the sequence of the variant defines a chain that produces a protein having substantially the same biological activity as the native urease. Such functionally equivalent variants that comprise substantial sequence variations are also encompassed by the invention. Thus, a functionally equivalent variant of the native urease protein will have a sufficient biological activity to be therapeutically useful. Methods are available in the art for determining functional equivalence. Biological activity can be measured using assays specifically designed for measuring activity of the native urease protein, as in Example 3. Additionally, antibodies raised against the biologically active native protein can be tested for their ability to bind to the functionally equivalent variant, where effective binding is indicative of a protein having a conformation similar to that of the native protein.

It will be appreciated by those skilled in the art that due to the degeneracy of the genetic code, a multitude of nucleic acids sequences encoding urease polypeptides of the invention may be produced, some of which may bear minimal sequence homology to known urease nucleic acid sequences. Such "silent variations" are one species of "conservatively modified variations", discussed below. The invention provides each and every possible variation of nucleic acid sequence encoding a polypeptide of the invention that could be made by selecting combinations based on possible codon choices. These combinations are made in accordance with the standard triplet genetic code as applied to the nucleic acid sequence encoding a urease protein polypeptide of the invention.

Urease polypeptides of the present invention include one or more conservatively modified variations (or simply "conservative variations") of the sequences of known urease polypeptide sequences. Such conservative variations comprise substitutions, additions or deletions that alter, add or delete a single amino acid or a small percentage of amino acids. One of ordinary skill in the art will recognize that an individual substitution, deletion, or addition that substitutes, deletes, or adds a single amino acid or a small percentage of amino acids (typically less than 5%, more typically less than 4%, 2%, 1%, or less) in a sequence typically constitutes conservative variations where such changes result in the deletion of an amino acid, addition of an amino acid, or substitution of an amino acid with a chemically similar amino acid.

Conservative substitution tables providing functionally similar amino acids are well known those of ordinary skill in the art. Table 1 sets forth six groups which contain amino acids that are conservative substitutions or conservative variations for one another.

TABLE 1

Conservative Substitution Groups

| | | | | |
|---|---|---|---|---|
| 1 | Alanine (A) | Serine (s) | Threonine (T) | |
| 2 | Aspartic Acid (D) | Glutamic Acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalnine (F) | Tyrosine (Y) | Tryptophan (W) | |

Additional groups of amino acids can also be formulated. For example, amino acids can be grouped by similar function or chemical structure or composition (e.g., acidic, basic, aliphatic, aromatic, sulfur-containing). For example, an aliphatic grouping may comprise: glycine, alanine, valine, leucine, isoleucine. Other groups containing amino acids that are conservative substitutions for one another include the following: (i) aromatic: phenylalanine, tyrosine, tryptophan; (ii) sulfur-containing: methionine, cysteine; (iii) basic: arginine, lysine, histidine; and (iv) acidic: aspartic acid, glutamic acid, asparagine, glutamine. See Creighton (1984) Proteins, W. H. Freeman and Company, for additional groupings of amino acids.

The urease protein sequences of the invention, including conservatively substituted sequences, can be present as part of larger polypeptide sequences such as occur upon the addition of one or more domains for purification of the protein (e.g., poly his segments, FLAG tag segments, etc.), e.g., where the additional functional domains have little or no effect on the activity of the urease protein portion of the protein, or where the additional domains can be removed by post synthesis processing steps, such as by treatment with a protease.

The addition of one or more nucleic acids or sequences that do not alter the encoded activity of a nucleic acid molecule of the invention, such as the addition of a non-functional sequence, is a conservative variation of the basic nucleic acid molecule, and the addition of one or more amino acid residues that do not alter the activity of a polypeptide of the invention is a conservative variation of the basic polypeptide. Both such types of additions are features of the invention. One of ordinary skill in the art will appreciate that many conservative variations of the nucleic acid constructs which are disclosed yield a functionally identical construct.

A variety of methods of determining sequence relationships can be used, including manual alignment, and computer assisted sequence alignment and analysis. This later approach is a preferred approach in the present invention, due to the increased throughput afforded by computer-assisted methods. A variety of computer programs for performing sequence alignment are available, or can be produced by one of skill.

As noted above, the sequences of the nucleic acids and polypeptides (and fragments thereof) employed in the subject invention need not be identical, but can be substantially identical (or substantially similar), to the corresponding sequence of a urease polypeptide or nucleic acid molecule (or fragment thereof) of the invention or related molecule. For example, the polypeptides can be subject to various changes, such as one or more amino acid or nucleic acid insertions, deletions, and substitutions, either conservative or non-conservative, including where, e.g., such changes might provide for certain advantages in their use, e.g., in their therapeutic or prophylactic use or administration or diagnostic application.

Alignment and comparison of relatively short amino acid sequences (less than about 30 residues) is typically straightforward. Comparison of longer sequences can require more sophisticated methods to achieve optimal alignment of two sequences. Optimal alignment of sequences for aligning a comparison window can be conducted by the local homology algorithm of Smith and Waterman (1981) *Adv Appl Math* 2:482, by the homology alignment algorithm of Needleman and Wunsch (1970) *J Mol Biol* 48:443, by the search for similarity method of Pearson and Lipman (1988) *Proc Nat'l Acad Sci* USA 85:2444, by computerized implementations of these algorithms (GAP, BESTFIT, FASTA and TFASTA in the Wisconsin Genetics Software Package Release 7.0, Genetics Computer Group, 575 Science Dr., Madison, Wis.; and BLAST, see, e.g., Altschul et al. (1977) *Nuc Acids Res* 25:3389–3402 and Altschul et al. (1990) *J Mol Biol* 215:403–410), or by inspection, with the best alignment (i.e., resulting in the highest percentage of sequence similarity or sequence identity over the comparison window) generated by the various methods being selected.

An exemplary algorithm that is suitable for determining percent sequence identity (percent identity) and sequence similarity is the FASTA algorithm, which is described in Pearson, W. R. & Lipman, D. J. (1988) *Proc Nat'l Acad Sci* USA 85:2444. See also, W. R. Pearson (1996) Methods Enzymology 266:227–258. Preferred parameters used in a FASTA alignment of DNA sequences to calculate percent identity are optimized, BL50 Matrix 15: −5, k-tuple=2; joining penalty=40, optimization=28; gap penalty=−12, gap length penalty=−2; and width=16.

It will be understood by one of ordinary skill in the art, that the above discussion of search and alignment algorithms also applies to identification and evaluation of polynucleotide sequences, with the substitution of query sequences comprising nucleotide sequences, and, where appropriate, selection of nucleic acid databases.

B. Associated Chemical Entity

The composition of the invention may comprise a chemical entity which is associated with the active agent to enhance the delivery of the active agent to the cancer cells. A wide variety of associated chemical entities are contemplated for use as described below.

B1. Polymers

The chemical entity may comprise a polymer including, for example, hydrophilic polymers and hydrophobic polymers, with hydrophilic polymers being preferred. The term "hydrophilic", as used herein, refers to a composition, substance or material, for example, a polymer, which may generally readily associate with water. Thus, although the hydrophilic polymers that may be employed in the present invention may have domains of varying type, for example, domains which are more hydrophilic and domains which are more hydrophobic, the overall nature of the hydrophilic polymers is preferably hydrophilic, it being understood, of course, that this hydrophilicity may vary across a continuum from relatively more hydrophilic to relatively less hydrophilic.

A wide variety of polymers may be employed in the present compositions and formulations. Generally, the polymer is one which has the desired hydrophilicity and/or hydrophobicity, and which may form matrices, as well as covalent attachments with targeting ligands, as described herein. The polymer may be crosslinked or non-crosslinked.

The terms "crosslink", "crosslinked" and "crosslinking", as used herein, generally refer to the linking of two or more compounds or materials, for example, polymers, by one or more bridges. The bridges, which may be composed of one or more elements, groups or compounds, generally serve to join an atom from a first compound or material molecule to an atom of a second compound or material molecule. The crosslink bridges may involve covalent and/or non-covalent associations. Any of a variety of elements, groups and/or compounds may form the bridges in the crosslinks, and the compounds or materials may be crosslinked naturally or through synthetic means.

In accordance with certain embodiments, the polymer, whether linear, star or branched, may be selected from the group consisting of a polyalkylene oxide, polyalkyleneimine, polyalkylene amine, polyalkene sulfide, polyalkylene sulfonate, polyalkylene sulfone, poly(alkylenesulfonylalkyleneimine) and copolymers thereof.

As noted above, depending on the particular polymer employed, the polymers may be relatively more hydrophilic or relatively more hydrophobic. Examples of suitable, relatively more hydrophilic polymers include, but are not limited to, polyethylene glycol, polypropylene glycol, branched polyethylene imine, polyvinyl pyrrolidone, polylactide, poly (lactide-co-glycolide), polysorbate, polyethylene oxide, poly(ethylene oxide-co-propylene oxide), poly(oxyethylated) glycerol, poly(oxyethylated) sorbitol, poly(oxyethylated glucose), polymethyloxazoline, polyethyloxazoline, polyhydroxyethyloxazoline, polyhydroxypropyloxazoline, polyvinyl alcohol, poly(hydroxyalkylcarboxylic acid), polyhydroxyethyl acrylic acid, polyhydroxypropyl methacrylic acid, polyhydroxyvalerate, polyhydroxybutyrate, polyoxazolidine, polyaspartamide, polysialic acid, and derivatives, mixtures and copolymers thereof.

Accordingly, a polymer, preferably hydrophilic, may be conjugated to the active agent, or other associated chemical entities disclosed herein, to enhance the delivery of the active agent to the cancer cells. The polymer-active agent conjugate is preferably administered in an amount effective to extend the blood circulation time and/or reduce the antigenicity and/or immunogenicity of said composition relative to native, or non-derivatized, active agent. Particularly preferred hydrophilic polymers include, but are not limited to, polyvinylpyrrolidone, polyvinylmethylether, polyhydroxypropyl methacrylamide, polyhydroxypropyl methacrylate, polyhydroxyethyl acrylate, polymethacrylamide, polydimethylacrylamide, polymethyloxazoline, polyethyloxazoline, polyhydroxyethyloxazolione, polyhydroxypropyoxazoline, polyaspartamide, and/or hydrophilic cellulose derivatives. A preferable hydrophilic polymer is polyethylene glycol having, e.g., a molecular weight between about 1,000 and 10,000 daltons. In one embodiment, the polyethylene glycol has a molecular weight between 1,000 and 5,000 daltons. Additional polymers contemplated for use in the invention are discussed in more detail in U.S. Pre-Grant Published No. 20020041898, published Apr. 11, 2002, which is incorporated by reference herein.

B2. Targeting Moiety

Targeting moieties are contemplated as chemical entities of the present invention, and bind to a defined, selected cell type or target cell population, such as cancer cells. Targeting moieties useful in this regard include antibodies and antibody fragments, peptides, and hormones. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also contemplated targeting moieties. Oligonucleotides, e.g., antisense oligonucleotides that are complementary to a portion of a target cell nucleic acid, may be used as targeting moieties in the present invention. Targeting moieties may also be oligonucleotides that bind to a target cell surface. Analogs of the above-listed targeting moieties that retain the ability to bind to a defined target cell population may also be used as targeting moieties.

Functional equivalents of the aforementioned targeting moieties are also useful as targeting moieties of the present invention. An exemplary targeting moiety functional equivalent is an organic chemical construct designed to mimic the proper configuration and/or orientation for targeting moiety target cell binding. Another targeting moiety functional equivalent is a short polypeptide that exhibits the binding affinity of the targeting moiety.

Preferred targeting moieties of the present invention are antibodies, peptides, oligonucleotides or the like, that are reactive with an antigen on the surface of a target cell. Both polyclonal and monoclonal antibodies which are either available commercially or described in the literature may be employed. The antibodies may be whole antibodies or fragments thereof. Monoclonal antibodies and fragments may be produced in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species.

In one embodiment of the invention, human monoclonal antibodies or humanized murine antibodies are used as targeting moieties. Humanized targeting moieties are capable of decreasing the immunoreactivity of the antibody or polypeptide in the host recipient, permitting an increase in the half-life and a reduction in adverse immune reactions. Murine monoclonal antibodies may be humanized by, e.g., genetically recombining the nucleotide sequence encoding the murine Fv region or the complementarity determining regions thereof with the nucleotide sequence encoding a human constant domain region and an Fc region. Murine residues may also be retained within the human variable region framework domains to ensure proper target site binding characteristics. A non-limiting example of a targeting moiety is the anti-α-2-GP antibody to brain glial cells (alpha-2-glycoprotein) which is described by Slepnev et al., Bioconjugate Chem. 3: 273–274 (1992). Genetically engineered antibodies for delivery of various active agents to cancer cells is reviewed in Bodey, B. (2001) Expert Opin Biol. Ther. 1(4):603–17.

In another embodiment of the invention, the targeting moiety is a ligand which is reactive with a receptor on the surface of the target cell. Thus, the targeting moiety may include without limitation hormones with affinity for a cellular binding component, any molecule containing a carbohydrate moiety recognized by a cellular binding component and drugs or small molecules that bind to a cellular binding component. The phrase "binding component" includes both receptor and acceptor molecules. Preferably, the binding component is a cell-surface binding component. In one embodiment, the targeting moiety is a naturally occurring protein, such as insulin, that binds to a target site. Cytokines, including interleukins and factors such as granulocyte/macrophage colony stimulating factor (GM-CSF) and tumor necrosis factor (TNF) are also specific targeting moieties, known to bind to specific cells expressing high levels of their receptors (Terlikowski, SJ (2002) Toxicology 174(3):143–152).

In order to decrease urease or other active agent exposure to non-target cells or tissues, targeting moieties may be screened to identify those that display minimal non-target reactivity, while retaining target specificity and reactivity. By reducing non-target exposure (and adverse non-target localization and/or toxicity), increased doses of urease or other active agent may be administered. This allows the administration of the highest possible concentration of urease or other therapeutic agent in order to maximize exposure of target cells, while remaining below the threshold of unacceptable non-target cell toxicity.

In certain embodiments of the invention, two or more active agent-targeting moiety conjugates are employed, wherein each conjugate includes a different targeting moiety, e.g., a different antibody species. Each of the utilized targeting moieties binds to a different target site region that may be associated with the same or a different target site. The active agent component of each administered conjugate may be the same or different. See, e.g., U.S. Pat. Nos. 4,867,962 and 5,976,535, each of which are incorporated by reference herein. In the practice of this embodiment of the invention, the target site accretion of active agent conjugate to the target site is improved, because each targeting moiety, e.g., antibody species, recognizes a different target site region, e.g., target site epitope. This alternative target site region approach provides more potential target site binding points for the active agent. Consequently, actual or effective target site saturation, e.g., via epitope saturation and/or steric hindrance, may be avoided. Thus, additive accumulation of active agent, e.g., urease, may be accomplished. Alternatively, or in combination, additional urease specific gene products may be employed as active agents, e.g., for the production of a catalytically active holoenzyme at the target site. An exemplary urease apoenzyme includes the gamma, beta and alpha subunits encoded by the bacterial ureABC genes (Burne, R. A. and Chen, Y. M. (2000) Microbes and Infection 2:533–542).

The patterns of cross-reactivity for monoclonal antibodies directed against a particular target site may be analyzed to identify a set of two or more target-specific monoclonal antibodies with non-overlapping cross-reactivity for use in a diagnostic or therapeutic application. The phrase "non-overlapping patterns of cross-reactivity" indicates that the non-target tissues bound by one antibody species differs substantially from the non-target tissues bound by another antibody species. The patterns of cross-reactivity differ to the extent necessary to proportionately reduce the exposure of active agent for therapeutic applications. Less antibody pair (or larger set of antibodies) overlap is preferred.

Antibodies may be screened by a variety of methods. Immunohistochemical analysis may be employed to determine reactivity with target tissue and cross-reactivity with non-target tissue. Tissues to which the antibody species bind may be identified by exposing the tissue to the antibody; washing the tissue to remove any unbound antibody; and detecting the presence of bound antibody. In vitro histochemical procedures are known in the art. See, e.g., Sanchez-lslas, E. and Leon-Olea, M. (2001) Nitric Oxide 5(4):302–16.

The composition of the present invention may also be of use in the treatment of hCG-secreting tumors. Because the placental trophoblast is the normal site of synthesis of hCG, it is understandable that both gestational and nongestational trophoblastic tumors synthesize and secrete hCG. Indeed, hCG measurements have been quite useful for the diagnosis of these tumors, staging the tumors, and for monitoring the effects of therapy. In addition, some nontrophoblastic tumors may produce hCG ectopically. hCG may act as a growth factor for some tumors (Melmed S. and Braunstein GD: Human chorionic gonadotropin stimulates proliferation of Nb 2 rat lymphoma cells. *J. Clin. Endocrinol. Metab* 56:1068–1070, (1983)). See, e.g., U.S. Pat. No. 6,448,022, which is incorporated by reference herein.

Therefore, according to one embodiment of the invention, the use of an anti-hCG antibody to target the active agent to a hCG-secreting tumor suppresses the growth of the hCG-secreting tumor. Thus, in certain embodiments, the chemical entity of the invention is a targeting moiety attached to an active agent and is an anti-tumor antigen antibody, an anti-hCG antibody or a ligand capable of binding specifically to cancer-cell surface receptors. The targeting moiety is, preferably, a polypeptide linked to the urease enzyme to form a fusion protein.

As noted above, in accordance with one embodiment of the invention, the active agent is directly conjugated to the targeting moiety. Alternatively, according to another embodiment of the invention, a two- or three-step approach is used to deliver the active agent to the cancer cells. Thus, the active agent may include a first binding partner which is able to interact with a second binding partner, and the chemical entity may include a targeting moiety which includes the second binding partner. These embodiments are described in more detail in Section III, below.

One of skill will appreciate that the targeting moieties of this invention and the active agents may be joined together in any order. Thus, where the targeting moiety is a polypeptide, the active agent may be joined to either the amino or carboxy termini of the targeting molecule. The targeting moiety may also be joined to an internal region of the active agent, or conversely, the active agent may be joined to an internal location of the targeting moiety, as long as the attachment does not interfere with the respective activities of the molecules.

The targeting moiety and the active agent may be attached by any of a number of means well known to those of skill in the art. Typically, the active agent is conjugated, either directly or through a linker (spacer), to the targeting moiety. However, where both the targeting moiety and the active agent are polypeptides, it may be preferable to recombinantly express the chimeric molecule as a single-chain fusion protein.

In one embodiment, the targeting moiety (e.g., αhEGFR IgG Ab) is chemically conjugated to the active agent or chemical entity (e.g., a drug, urease or liposome). Means of chemically conjugating molecules are well known to those of skill.

The procedure for attaching an agent to an antibody or other polypeptide targeting molecule will vary according to the chemical structure of the agent. Polypeptides typically contain a variety of functional groups; e.g., carboxylic acid (COOH) or free amine (—NH2) groups, which are available for reaction with a suitable functional group on an active agent to bind the targeting moiety thereto.

Alternatively, the targeting moiety and/or active agent may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting moiety to the active agent. The linker is capable of forming covalent bonds to both the targeting moiety and to the active agent. Suitable linkers are well known to those of skill in the art and include, but are not limited to, straight or branched-chain carbon linkers, heterocyclic carbon linkers, or peptide linkers. Where the targeting moiety and the active agent molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting moiety, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (see U.S. Pat. No. 4,671,958). Procedures for generation of free sulfhydryl groups on polypeptide, such as antibodies or antibody fragments, are also known (see U.S. Pat. No. 4,659,839).

Many procedure and linker molecules for attachment of various compounds including radionuclide metal chelates, toxins and drugs to proteins, such as antibodies, are known (see, e.g., European Patent Application No.188, 256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071–4075). In particular, production of various immunotoxins is well-known within the art and can be found, for example, in "Monoclonal Antibody-Toxin Conjugates: Aiming the Magic Bullet," Thorpe et al., *Monoclonal Antibodies in Clinical Medicine*, Academic Press, pp. 168–190 (1982), Waldmann (1991) *Science,* 252: 1657, U.S. Pat. Nos. 4,545,985 and 4,894,443.

In some circumstances, it is desirable to free the active agent molecule from the targeting moiety when the chimeric molecule has reached its target site. Therefore, chimeric conjugates comprising linkages which are cleavable in the vicinity of the target site may be used when the effector is to be released at the target site. Cleaving of the linkage to release the agent from the targeting moiety may be prompted by enzymatic activity or conditions to which the conjugate is subjected either inside the target cell or in the vicinity of the target site. It should be appreciated that when the target site is a tumor, a linker which is cleavable under conditions present at the tumor site (e.g. when exposed to tumor-associated enzymes or acidic pH) may be used.

A number of different cleavable linkers are known to those of skill in the art (see U.S. Pat. Nos. 4,618,492; 4,542,225, and 4,625,014.) The mechanisms for release of an active agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to targeting moieties, one skilled in the art will be able to determine a suitable method for attaching a given agent to a selected targeting moiety.

Where the targeting moiety and/or the active agent is relatively short, they may be synthesized using standard chemical peptide synthesis techniques. Where both molecules are relatively short, the chimeric molecule may be synthesized as a single contiguous polypeptide. Alternatively, the targeting moiety and the active agent may be synthesized separately and then fused by condensation of the amino terminus of one molecule with the carboxyl terminus of the other molecule, thereby forming a peptide bond. Alternatively, the targeting moiety and active agent molecules may each be condensed with one end of a peptide spacer molecule, thereby forming a contiguous fusion protein.

Solid phase synthesis in which the C-terminal amino acid of the sequence is attached to an insoluble support followed by sequential addition of the remaining amino acids in the sequence is contemplated for one embodiment for the method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology. Vol. 2: Special Methods in Peptide Synthesis, Part A.*, Merrifield, et al. *J. Am. Chem. Soc.,* 85: 2149–2156 (1963), and Stewart et al., *Solid Phase Peptide Synthesis*, 2nd ed. Pierce Chem. Co., Rockford, Ill. (1984).

In a preferred embodiment, the chimeric fusion proteins of the present invention are synthesized using recombinant DNA methodology. Generally, this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention may be prepared by any suitable method, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.,* 22: 1859–1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule, such as the folding, net charge, or hydrophobicity.

The nucleic acid sequences encoding the fusion proteins may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, R. Scopes (1982) *Protein Purification*, Springer-Verlag, N.Y.; Deutscher (1990) *Methods in Enzymology Vol.* 182: *Guide to Protein Purification*., Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the targeted fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, Debinski et al. (1993) *J. Biol. Chem.,* 268: 14065–14070; Kreitman and Pastan (1993) *Bioconjug. Chem.,* 4: 581–585; and Buchner, et al. (1992) *Anal. Biochem.,* 205: 263–270).

One of skill would recognize that modifications can be made to the targeted fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

B3. Entrapped Active Agents

In certain embodiments, the invention contemplates the use of vesicles such as liposomes and/or nanocapsules as chemical entities for the delivery of an active agent or active agents, e.g., urease to cancer cells. Such formulations may be preferred for the introduction of pharmaceutically-acceptable formulations of the polypeptides, pharmaceuticals, and/or antibodies disclosed herein. The formation and use of liposomes is generally known to those of skill in the art. (See, e.g., Backer, M. V., et al. (2002) *Bioconjug Chem* 13(3):462–7). In a preferred embodiment, the disclosed composition may be entrapped in a liposome.

Nanocapsules can generally entrap compounds in a stable and reproducible way (Whelan, J. (2001) *Drug Discov Today* 6(23):1183–84). To avoid side effects due to intracellular polymeric overloading, such ultrafine particles (sized around 0.1 µm) may be designed using polymers able to be degraded in vivo. Biodegradable polyisobutylcyanoacrylate nanoparticles that meet these requirements are contemplated for use in the present invention, and such particles may be easily made, as described in, e.g., Lambert, G., et al. (2001) *Int J Pharm* 214(1–2):13–6. Methods of preparing polyalkyl-cyano-acrylate nanoparticles containing biologically active substances and their use are described in U.S. Pat. Nos. 4,329,332, 4,489,055 and 4,913,908. Nanocapsules are available commercially from sources such as Capsulution, Inc. (www.capsulution.com).

Pharmaceutical compositions containing nanocapsules for the delivery of active agents are described in U.S. Pat. Nos. 5,500,224, 5,620,708 and 6,514,481. U.S. Pat. No. 5,500,224 describes a pharmaceutical composition in the form of a colloidal suspension of nanocapsules comprising an oily phase consisting essentially of an oil containing dissolved therein a surfactant, and suspended therein a plurality of nanocapsules having a diameter of less than 500 nanometers. U.S. Pat. No. 5,620,708 describes compositions and methods for the administration of drugs and other active agents. The compositions comprise an active agent carrier particle attached to a binding moiety which binds specifically to a target molecule present on the surface of a mammalian enterocyte. The binding moiety binds to the target molecule with a binding affinity or avidity sufficient to initiate endocytosis or phagocytosis of the particulate active agent carrier so that the carrier will be absorbed by the enterocyte. The active agent will then be released from the carrier to the host's systemic circulation. In this way, degradation of degradation-sensitive drugs, such as polypeptides, in the intestines can be avoided while absorption of proteins and polypeptides from the intestinal tract is increased. Alternatively, the invention contemplates release of the active agent in the environment surrounding the target cell. For example, in one embodiment, urease is released from the nanocapsule following target moiety binding to the target cell, such that urease is released into the microenvironment surrounding the target cell, e.g., a tumor cell. U.S. Pat. Nos. 6,379,683 and 6,303,150 describe methods of making nanocapsules and the use thereof, and are incorporated herein by reference.

Thus, in one embodiment of the invention, the contacting includes adding to the cells a conjugate comprising a targeting moiety and a first coil-forming peptide characterized by a selected charge and an ability to interact with a second, oppositely charged coil-forming peptide to form a stable α-helical coiled-coil heterodimer. Subsequently, a liposome is added to the cells. The liposome comprises an exterior surface and an internal compartment; an active agent, e.g., urease, located within the internal compartment of the liposome; and a plurality of second peptides, wherein each second peptide is connected to the exterior surface of the liposome.

In another embodiment, described in detail below, the contacting includes adding liposomes to the cells, wherein the liposomes have the active agent, e.g., urease, in entrapped form, and outer surfaces of the liposome includes a cell targeting moiety effective to bind specifically to a target surface, and a hydrophilic polymer coating effective to shield the targeting moiety from interaction with the target surface. The hydrophilic polymer coating may be made up of polymer chains which are covalently linked to surface lipid components in the liposomes through releasable linkages. In this embodiment, a releasing agent is added to the tumor cells in an amount effective to cause release of a substantial portion of the linkages in the added liposomes, thereby exposing the targeting moiety to the target surface. The releasable linkages may be reducible chemical linkages such as disulfide, ester and peptide linkages. Preferably, the affinity moiety is effective to bind specifically to a cancer-specific antigen.

According to this embodiment of the invention, a method of liposome-based therapy for a mammalian subject is contemplated. The method includes systemically administering to the subject, e.g., intravenously administering, liposomes having a surface-bound targeting moiety and a hydrophilic polymer coating. The hydrophilic polymer coating, comprised of releasably attached polymer chains, is effective to shield the targeting moiety from interaction with its target. Preferred hydrophilic polymers are discussed above. The administered liposomes are allowed to circulate systemically until a desired biodistribution of the liposomes is achieved. A releasing agent, as described below, is administered to the subject in an amount effective to cause cleaving of a substantial portion, e.g., greater than about 50%, preferably greater than about 70%, and more preferably greater than about 90% of the releasable linkages in the administered liposomes. The targeting moiety is exposed upon release of the hydrophilic polymer chain for interaction with its target.

In a preferred embodiment, the liposomes are used for treatment of a solid tumor. The liposomes include urease, and optionally, an additional active agent, e.g., an anti-tumor drug, in entrapped form and are targeted to the tumor region by a targeting moiety effective to bind specifically to a tumor-specific antigen. In an exemplary method, liposomes are targeted to the vascular endothelial cells of tumors by including a VEGF ligand in the liposomes, for selective attachment to Flk-1,2 receptors expressed on the proliferating tumor endothelial cells (Niederman, T. M., et al. (2002) *Proc Natl Acad Sci* 99(10):7009–14).

Preferably, the liposomes have a size between about 30–400 nm. Liposomes in this size range have been shown to be able to enter tumors through "gaps" present in the endothelial cell lining of tumor vasculature (Maruyama, K, et al. (1999) *Adv Drug Deliv Rev* 40(1–2):89–102).

Following administration of the liposomes, e.g., intravenous administration, and after sufficient time has elapsed to allow the liposomes to distribute through the subject and bind to the tumor, a releasing agent is administered to the subject to release the hydrophilic surface coating from the liposomes. Release of the surface coating is effective to expose the targeting moiety to allow binding of the liposomes to the target cells. In one embodiment, the hydrophilic surface coating is attached to the liposomes by pH sensitive linkages. The linkages are released after the liposomes bind to the tumor.

The liposomes in any of the embodiments described above may, optionally, include one or more entrapped anti-tumor drugs or imaging agents or both. The liposomes may be added and allowed to distribute, after which a releasing agent can be administered to release the hydrophilic surface coating to expose the attached targeting moiety and initiate binding. Thus, the entrapped anti-tumor drug or imaging agent or both are specifically and locally administered to the target. Exemplary anti-cancer drugs are described in Section III.A. below. Exemplary imaging agents for use in the method of the invention are described in Section III.B. below. Liposomes may be prepared and administered as described in U.S. Pat. No. 6,043,094, which is incorporated herein by reference.

Additional delivery agents such as small unilamellar vesicles (SUV's), as described in U.S. Pat. No. 6,180,114, which is incorporated herein by reference in its entirety, may be employed in the present invention.

B4. Active Agent Modulators

Active agent modulators are also contemplated as associated chemical entities by the instant invention. A preferred active agent modulator is a urease modulator. A "urease modulator" is either an inhibitor of urease or an enhancer of urease. The modulator in the compositions (e.g., pharmaceutical compositions) accordingly may be selected from among all or portions of urease polynucleotide sequences, urease antisense molecules, urease polypeptides, protein, peptide, or organic modulators of urease bioactivity, such as inhibitors, antagonists (including antibodies) or agonists. Preferably, the modulator is active in treating a medical condition that is mediated by, or ameliorated by, urease expression or urease activity.

An "inhibitor of urease" comprises a molecule or group of molecules that interferes with: (1) the expression, modification, regulation, activation or degradation of urease: or (2) one or more of the normal functions of urease, including the hydrolysis of urea leading to the production of carbamate and ammonia. An inhibitor "acts directly on urease" when the inhibitor binds to urease via electrostatic or chemical interactions. Such interactions may or may not be mediated by other molecules. An inhibitor acts "indirectly on urease" when its most immediate effect is on a molecule other than urease which influences the expression, activation or functioning of urease.

Urease inhibitors serve to slow the conversion of urea to ammonium ions. Urease inhibitors include but are not limited to hydroxamic acid derivatives (e.g., acetohydroxamic acid), phosphoramide derivatives (e.g., flurofamide), phosphates, thiols (e.g., 2-mercaptoethanol etc.), boric acid, halogen compounds (e.g., fluorides etc.), and cassia bark extract. Additional urease inhibitors are known to those of skill in the art and are described in U.S. Pat. No. 4,824,783 (Apr. 25, 1989) which is incorporated herein by reference.

An "enhancer of urease" comprises a molecule or group of molecules that enhances: (1) the expression, modification, regulation or activation of urease; or (2) one or more of the normal functions of urease. An enhancer "acts directly on urease" when the enhancer binds to urease via electrostatic or chemical interactions. Such interactions may or may not be mediated by other molecules. An enhancer acts "indirectly on urease" when its most immediate effect is on a molecule other than urease which influences the expression, activation or functioning of urease.

C. Additional Active Agents

Additional active agents may also be included in the composition of the invention. The additional active agents, e.g., an anti-tumor agent (an agent active against proliferating cells), may be utilized in the composition prior to, concurrently with, or subsequent to the cells being contacted with a first active agent. For example, after urease has been targeted to the tumor cells, it may have the ability to modulate or regulate the tumor external environment, e.g., through pH changes. Active agents, e.g., anti-tumor agents that favor a basic environment will then be more efficacious.

In certain embodiments, substrates that are capable of being enzymatically processed by urease are contemplated for use as active agents. Preferably, the active agent is a substrate that urease may utlilize to form ammonium ions, e.g., urea.

Exemplary anti-tumor agents include cytokines and other moieties, such as interleukins (e.g., IL-2, IL-4, IL-6, IL-12 and the like), transforming growth factor-beta, lymphotoxin, tumor necrosis factor, interferons (e.g., gamma-interferon), colony stimulating factors (e.g., GM-CSF, M-CSF and the like), vascular permeability factor, lectin inflammatory response promoters (selectins), such as L-selectin, E-selectin, P-selectin, and proteinaceous moieties, such as C1q and NK receptor protein. Additional suitable anti-tumor agents include compounds that inhibit angiogenesis and therefore inhibit metastasis. Examples of such agents include protamine medroxyprogesteron, pentosan polysulphate, suramin, taxol, thalidomide, angiostatin, interferon-alpha, metalloproteinase inhibitors, platelet factor 4, somatostatin, thrombospondin. Other representative and non-limiting examples of active agents useful in accordance with the invention include vincristine, vinblastine, vindesine, busulfan, chlorambucil, spiroplatin, cisplatin, carboplatin, methotrexate, adriamycin, mitomycin, bleomycin, cytosine arabinoside, arabinosyl adenine, mercaptopurine, mitotane, procarbazine, dactinomycin (antinomycin D), daunorubicin, doxorubicin hydrochloride, taxol, plicamycin, aminoglutethimide, estramustine, flutamide, leuprolide, megestrol acetate, tamoxifen, testolactone, trilostane, amsacrine (m-AMSA), asparaginase (L-asparaginase), etoposide, blood products such as hematoporphyrins or derivatives of the foregoing. Other examples of active agents include genetic material such as nucleic acids, RNA, and DNA of natural or synthetic origin, including recombinant RNA and DNA. DNA encoding certain proteins may be used in the treatment of many different types of diseases. For example, tumor necrosis factor or interleukin-2 genes may be provided to treat advanced cancers; thymidine kinase genes may be provided to treat ovarian cancer or brain tumors; and interleukin-2 genes may be provided to treat neuroblastoma, malignant melanoma or kidney cancer. Additional active agents contemplated for use in the present invention are described in U.S. Pat. No. 6,261,537, which is incorporated by reference in its entirety herein. Anti-tumor agents and screens for detecting such agents are reviewed in Monga, M. and Sausville, E. A. (2002) *Leukemia* 16(4):520–6.

In certain embodiments, the active agent is a weakly basic anti-tumor compound whose effectiveness is reduced by a higher intracellular/lower extracellular pH gradient in a solid tumor. Exemplary weakly basic anti-tumor compounds include doxorubicin, daunorubicin, mitoxanthrone, epirubicin, mitomycin, bleomycin, vinca alkaloids, such as vinblastine and vincristine, alkylating agents, such as cyclophosphamide and mechlorethamine hydrochloride, and antrineoplastic purine and pyrimidine derivatives.

In one embodiment of the invention, the composition includes urease, and lacks substantially any cytokines, e.g. tumor necrosis factor and/or interferons. In this embodiment, urease alone, or with active agents other than cytokines, preferably in combination with small molecule anti-tumor agents, is effective to inhibit cancer cell growth. Thus, in this embodiment, the composition may or may not act in concert with endogenous or native cytokines present in the subject being treated, but the composition being administered does not contain additional, exogenous cytokines.

D. Imaging Agents

Likewise, imaging agents may be included in the composition or in additional compositions. Suitable imaging agents include commercially available agents used in positron emission tomography (PET), computer assisted tomography (CAT), single photon emission computerized tomography, x-ray, fluoroscopy, and magnetic resonance imaging (MRI).

Imaging agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached or entrapped using a variety of techniques as described above, and may be present in any orientation. See, e.g., U.S. Pat. Nos. 6,159,443 and 6,391,280, both of which are expressly incorporated by reference herein.

Contrast agents according to the present invention are useful in the imaging modalities, such as X-ray contrast agents, light imaging probes, spin labels or radioactive units.

Examples of suitable materials for use as contrast agents in MRI include the gadolinium chelates currently available, such as diethylene triamine pentaacetic acid (DTPA) and gadopentotate dimeglumine, as well as iron, magnesium, manganese, copper, and chromium.

Examples of materials useful for CAT and x-rays include iodine based materials, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

Air and other gases can be incorporated for use in ultrasound imaging. These agents can be detected using standard techniques available in the art and commercially available equipment.

According to one embodiment of the invention, the cancer cells are contacted with an imaging agent before or after, or both before and after being contacted with the active agent. For example, after urease has been targeted to the tumor cells, it may have the ability to modulate or regulate the tumor external environment, e.g., through pH changes. Imaging agents that favor a basic environment will then be more efficacious.

Both luminescent cyclen-based lanthamide chelates and those primarily yielding magnetic resonance signatures have been shown to be sensitive to changes in pH. Luminescent probes used for sensing pH changes typically detect changes in the fluorescence lifetime of the lanthamide ion as a function of pH. Analogously, magnetic resonance contrast agents which modulate the water proton relaxivity via changes in pH are useful in the instant invention. In both cases, by changing the pH in a given system, one can envision agents with enhanced contrast.

Accordingly, a pH sensitive contrast agent is utilized at or near the cancer cell. The cancer cell or cells are also exposed to a urease composition containing urease enzyme to cause a change in pH at or near the cancer cell. In this way, a change in pH causes the nuclear magnetic resonance relaxation properties of water protons or other nuclei in the aqueous medium to be changed in a manner that is reflective of pH. Examples of pH sensitive contrast agents that may be utilized include those agents that contain a lanthamide metal, such as Ce, Pr, Nd, Sm, Eu, Gd, Db, Dy, Ho, Er, Tm, Yb, and the like, or another paramagnetic element, such as Fe, Mn, 17O, or the like. Specific contrast agents that may be utilized include H (2)(17)0, GdDOTA-4AmP(5-) which is described in *Magn Reson Med.* 2003 February;49(2): 249–57, and Fe(III)meso-tetra(4-sulfonatophenyl)porphine (Fe-TPPS4) as described in Helpern et al. (1987) *Magnetic Resonance in Medicine* 5:302–305 and U.S. Pat. No. 6,307,372, which is incorporated herein by reference. In addition, Gd based with polyion, as described in Mikawa et al. *Acad. Radiol* (2002) 9(suppl 1):S109–S1111, may be used in the invention.

As another alternative, a shift reagent may be provided in the aqueous medium surrounding the cancer cell. The shift reagent is configured such that a change in pH affects the chemical shift properties of the water protons or other nuclei in a manner that is reflective of pH. The change in chemical shift properties may then be measured using nuclear magnetic resonance to determine whether the active agent is biologically active. Examplary shift reagents that may be used include those containing a lanthamide metal, such as Ce, Pr, Nd, Sm, Eu, Gd, Db, Dy, Ho, Er, Tm, or Yb, or another paramagnetic element. Examples of specific shift reagents that may be utilized include Tm(DOTP) (5-), the thulium (III) complex of 1,4,7,10-tetraazacylododecane-N, N',N",N'''-tetra(methylenephospate). Dy(PPP) (2)(7)-dysprosium tripolyphosphate, and the like.

In one embodiment of the invention, a dual-contrast-agent strategy using two gadolinium agents, such as the pH-insensitive GdDOTP(5-) and the pH-sensitive GdDOTA-4AmP(5-), may be utilized to generate pH maps by MRI, as described in *Magn Reson Med* (2003) February;49(2): 249–57.

Preferred agents for use with PET scan include 13N and fluorodeoxyglucose (FDG).

E. Composition Formulation

As noted above, the compositions of the invention comprise an active agent and, optionally, an associated chemical entity. For example, a urease polypeptide or urease polynucleotide, and/or comprise a chemical or biological compound that is active as a modulator of urease expression or urease activity. In addition, a biocompatible pharmaceutical carrier, adjuvant, or vehicle may also be included.

The composition may also include other nucleotide sequences, polypeptides, drugs, or hormones mixed with excipient(s) or other pharmaceutically acceptable carriers. Compositions other than pharmaceutical compositions optionally comprise liquid, i.e., water or a water-based liquid.

Pharmaceutically acceptable excipients to be added to pharmaceutical compositions also are well-known to those who are skilled in the art, and are readily available. The choice of excipient will be determined in part by the particular method used to administer the product according to the invention. Accordingly, there is a wide variety of suitable formulations for use in the context of the present invention.

Techniques for formulation and administration of pharmaceutical compositions may be found in Remington's Pharmaceutical Sciences, 19th Ed., 19th Ed., Williams & Wilkins, 1995, and are well known to those skilled in the art. The choice of excipient will be determined in part by the particular method used to administer the product according to the invention. Accordingly, there is a wide variety of suitable formulations for use in the context of the present invention. The following methods and excipients are merely exemplary and are in no way limiting.

The pharmaceutical compositions of the present invention may be manufactured using any conventional method, e.g., mixing, dissolving, granulating, levigating, emulsifying, encapsulating, entrapping, melt-spinning, spray-drying, or lyophilizing processes. However, the optimal pharmaceutical formulation will be determined by one of skill in the art depending on the route of administration and the desired dosage. Such formulations may influence the physical state, stability, rate of in vivo release, and rate of in vivo clearance of the administered agent. Depending on the condition being treated, these pharmaceutical compositions may be formulated and administered as described in Section III below.

The pharmaceutical compositions are formulated to contain suitable pharmaceutically acceptable carriers, and may optionally comprise excipients and auxiliaries that facilitate processing of the active compounds into preparations that can be used pharmaceutically. The administration modality will generally determine the nature of the carrier. For example, formulations for parenteral administration may comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hank's-solution, Ringer's solutions, or physiologically buffered saline. For tissue or cellular administration, penetrants appropriate to the particular barrier to be permeated are used in the formulation. Such penetrants are generally known in the art. For preparations comprising proteins, the formulation may include stabilizing materials, such as polyols (e.g., sucrose) and/or surfactants (e.g., nonionic surfactants), and the like.

Alternatively, formulations for parenteral use may comprise suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Emulsions, e.g., oil-in-water and water-in-oil dispersions, can also be used, optionally stabilized by an emulsifying agent or dispersant (surface-active materials; surfactants). Liposomes, as described above, containing the active agent may also be employed for parenteral administration.

Alternatively, the pharmaceutical compositions comprising the agent in dosages suitable for oral administration can be formulated using pharmaceutically acceptable carriers well known in the art. The preparations formulated for oral administration may be in the form of tablets, pills, capsules, cachets, lozenges, liquids, gels, syrups, slurries, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets. Oral formulations may employ liquid carriers similar in type to those described for parenteral use, e.g., buffered aqueous solutions, suspensions, and the like.

These preparations may contain one or more excipients, which include, without limitation: a) diluents such as sugars, including lactose, dextrose, sucrose, mannitol, or sorbitol; b) binders such as magnesium aluminum silicate, starch from com, wheat, rice, potato, etc.; c) cellulose materials such as methyl cellulose, hydroxypropyhnethyl cellulose, and sodium carboxymethyl cellulose, polyvinyl pyrrolidone, gums such as gum arabic and gum tragacanth, and proteins such as gelatin and collagen; d) disintegrating or solubilizing agents such as cross-linked polyvinyl pyrrolidone, starches, agar, alginic acid or a salt thereof such as sodium alginate, or effervescent compositions; e) lubricants such as silica, talc, stearic acid or its magnesium or calcium salt, and polyethylene glycol; f) flavorants and sweeteners; g) colorants or pigments, e.g., to identify the product or to characterize the quantity (dosage) of active agent; and h) other ingredients such as preservatives, stabilizers, swelling agents, emulsifying agents, solution promoters, salts for regulating osmotic pressure, and buffers.

The pharmaceutical composition may be provided as a salt of the active agent, which can be formed with many acids, including but not limited to hydrochloric, sulfuric, acetic, lactic, tartaric, malic, succinic, etc. Salts tend to be more soluble in aqueous or other protonic solvents that are the corresponding free base forms.

As noted above, the characteristics of the agent itself and the formulation of the agent can influence the physical state, stability, rate of in vivo release, and rate of in vivo clearance of the administered agent. Such pharmacokinetic and pharmacodynamic information can be collected through preclinical in vitro and in vivo studies, later confirmed in humans during the course of clinical trials. Guidance for performing human clinical trials based on in vivo animal data may be obtained from a number of sources, including, e.g., http://www.clinicaltrials.gov. Thus, for any compound used in the method of the invention, a therapeutically effective dose in mammals, particularly humans, can be estimated initially from biochemical and/or cell-based assays. Then, dosage can be formulated in animal models to achieve a desirable circulating concentration range that modulates active agent expression or activity. As human studies are conducted, further information will emerge regarding the appropriate dosage levels and duration of treatment for various diseases and conditions.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population).

III. Method of the Invention

Another aspect of the present invention includes a method of inhibiting the growth of cancer cells. The method employs one or more of the components of the composition described in Section II, above, and/or in Sections IV–VII, below. The method includes exposing the cells to urease as an active agent in an amount effective to inhibit growth of the cancer cells.

A. Exposing Cancer Cells to an Active Agent

The urease composition, e.g., urease alone or urease in combination with a chemical entity effective to enhance the delivery of the enzyme to cancer cells, may be delivered to the cancer cells by a number of methods known in the art. In therapeutic applications, the composition is administered to a patient having cancer cells in an amount sufficient to inhibit growth of the cancer cell(s). The pharmaceutical compositions of the invention can be exposed to the cancer cells by administration by a number of routes, including without limitation, parenteral, enteral, transepithelial, transmucosal, transdermal, and/or surgical.

Parenteral administration modalities include those in which the composition is administered by, for example, intravenous, intraarterial, intraperitoneal, intramedullary, intramuscular, intraarticular, intrathecal, and intraventricular injections, subcutaneous, intragonadal or intratumoral needle bolus injections, or prolonged continuous, pulsatile or planned perfusions or microinfusions using the appropriate pump technology. Enteral administration modalities include, for example, oral (including buccal and sublingual) and rectal administration. Transepithelial administration modalities include, for example, transmucosal administration and transdermal administration. Transmucosal administration includes, for example, enteral administration as well as nasal, inhalation, and deep lung administration, vaginal administration, and rectal administration. Transdermal administration includes passive or active transdermal or transcutaneous modalities, including, for example, patches and iontophoresis devices, as well as topical application of pastes, salves, or ointments. Surgical techniques include implantation of depot (reservoir) compositions, osmotic pumps, and the like.

Single or multiple administrations of the active agent may be administered depending on the dosage and frequency as required and tolerated by the subject. In any event, the composition should provide a sufficient quantity of the active agent of the invention to effectively treat the subject.

It will be appreciated by one of skill in the art that there are some regions that are not heavily vascularized or that are protected by cells joined by tight junctions and/or active transport mechanisms which reduce or prevent the entry of macromolecules present in the blood stream. Thus, for example, systemic administration of therapeutics to treat gliomas, or other brain cancers, may be constrained by the blood-brain barrier which resists the entry of macromolecules into the subarachnoid space. In these types of tumors, the therapeutic composition may preferably be administered directly to the tumor site. Thus, for example, brain tumors can be treated by administering the therapeutic composition directly to the tumor site, e.g., through a bolus injection, microinfusion, or a surgically implanted catheter.

The exposing may include visualizing the cancer cell or tumor with an image guidance tool, e.g., as described in Enhanced Magnetic Resonance Imaging, V. M. Runge, ed., C. V. Mosby Co. (1989) for MRI; e.g., in EP 188,256; Kozak et al., TIBTEC October 1986, 262; Radiotracers for Medical Applications, CRC Press, Boca Raton, Fla., for radiodiagnostics and/or for radiotherapy; in Positron Emission Tomography of the Brain, Springer Verlag 1983, for PET; and in J. W. Nowicky et al., "Macroscopic UV-Marking through Affinity," J. Tumor Marker Oncology 31, 463–465 (1988). Thus, any of a variety of diagnostic agents can be incorporated within the compositions, which can locally or systemically deliver the incorporated agents following administration to a patient.

Imaging agents, as described above, can be used to allow one to monitor tumor treatment following administration of the compositions in a patient. For example, they are typically administered prior to the performance of the imaging procedure. It is also possible for the administration to be simultaneous with the imaging where desired, e.g., in pharmacokinetic studies. The optimum time period required for localization at the target site and optimum image enhancement will also vary with active agent and/or conjugate and/or tissue and/or imaging modality, and will also be routinely determinable. Typically, imaging will occur prior to significant clearance of the active agent from the site, which time period can also be routinely determined by those of skill in the art. In certain embodiments, active agents or conjugates will be administered 15 minutes to 4 hours prior to performing the imaging procedure, since the active agents may be localized rapidly to their target sites and then, optionally, cleared rapidly therefrom, as discussed further below.

In one embodiment of the invention, the exposing includes interrogating the subject with a diagnostic tool capable of detecting changes in extracellular pH in a subject's tissue, and identifying a tissue region within the subject that shows a selected elevation in extracellular pH following the administering. Based on the identification, the exposing can be repeated until a selected change in extracellular pH within the entire solid tumor is achieved.

In one embodiment of the invention, the exposing includes administering the active agent composition parenterally to the subject other than by direct injection. The active agent may be derivatized as discussed in Section II, above.

As discussed above, urease catalyzes the hydrolysis of urea, leading to the production of carbamate and ammonia. In an aqueous environment, the carbamate rapidly and spontaneously decomposes to yield a second molecule of ammonia and one of carbon dioxide (FIG. 1). Urease has a wide variety of functions. Its primary environmental role is to allow organisms to use external and internally generated urea as a nitrogen source. In plants urease may participate in the systemic nitrogen transport pathways and possibly act as a toxic defense protein.

The substrate for urease is urea, which is produced in the liver, carried in the bloodstream to the kidneys, and excreted in urine. Serum concentrations of urea in healthy humans are typically between one and 10 mM, but urea levels in urine may exceed 0.5 M (Merck Manual of Diagnosis and Therapy, Merck and Co., Inc., Rahway, N.J., 1999). Urea is also present in the secretions of the major and minor exocrine glands at concentrations approximately equivalent to serum, so a large proportion of circulating urea is translocated onto cell surfaces by secretory systems, or in tissue exudates (Burne, R. A., and Chen, Y. M., *Microbes and Infection*, 2, 2000; 533–542). For example, adult humans secrete almost 1 liter of saliva per day containing 1–10 mM urea, and approximately 20–25% of all urea produced enters the intestinal tract rather than exiting the body in urine (Visek, W. J., *Fed. Proc.* 31 (1972) 1178–1193). There is no apparent active efflux mechanism for exocrine secretion of urea, so it is believed that the uncharged urea molecule simply follows water through the cells and tight junctions of the epithelium. As a consequence, the surfaces of cells in the human body are bathed in a fluid which contains urea (McLean R. J. C., et al. CRC, *Crit. Rev. Microbiol.* 16 (1988) 37–79).

B. Two- and Three-Stage Exposure

As noted above, in accordance with one embodiment of the invention, the active agent is directly conjugated to the targeting moiety. Alternatively, according to another embodiment of the invention, a two-step approach is used to deliver the active agent to the tumor cells. Preferably, the tumor cells are contained within a subject. The two-step approach has the advantage of decoupling the pharmacokinetics of the active agent from that of the targeting moiety. The targeting moiety is permitted to accrete to target sites while conjugated to a first binding partner, e.g., a coil-forming peptide. Following accretion of the targeting moiety, substantially all of the non-targeted conjugate may be cleared from the subject's circulation. The active agent may then be administered as a conjugate to the complementary binding partner member, e.g., a second coil-forming peptide.

Any two-stage system known in the art may be used, such as biotin, haptens, etc. having a high affinity binding partner, e.g., avidin, specific antibodies, etc. See, e.g., U.S. Pat. Nos. 6,190,923, 6,187,285, and 6,183,721.

A preferred two-stage system includes a coiled-coil system. Thus, in certain embodiments of the invention employing a two-step approach as described above, a first conjugate comprising a targeting moiety and a first coil-forming peptide characterized by a selected charge and an ability to interact with a second, oppositely charged coil-forming peptide to form a stable α-helical coiled-coil heterodimer is added to the tumor cells. An exemplary method for conjugating an antibody targeting moiety to a coil-forming peptide is described in Example 4.

Subsequently a second conjugate comprising the second coil-forming peptide and the active agent is added to the cells. A preferable active agent is urease. An exemplary method for the conjugation of jack bean urease to a coil-forming peptide is described in Example 2.

When a first coil-forming peptide and a second coil-forming peptide are mixed together under conditions favoring the formation of α-helical coiled-coil heterodimers, they interact to form a two-subunit α-helical coiled-coil heterodimeric complex. Peptides in an α-helical coiled-coil conformation interact with one another in a characteristic manner that is determined by the primary sequence of each peptide. The tertiary structure of an α-helix is such that seven amino acid residues in the primary sequence correspond to approximately two turns of the α-helix. Accordingly, a primary amino acid sequence giving rise to an α-helical conformation may be broken down into units of seven residues each, termed "heptads". The heterodimer-subunit peptides are composed of a series of heptads in tandem. When the sequence of a heptad is repeated in a particular heterodimer-subunit peptide, the heptad may be referred to as a "heptad repeat", or simply "repeat".

A first coil-forming peptide and second coil-forming peptide may assemble into a heterodimer coiled-coil helix (coiled-coil heterodimer) in either parallel or antiparallel configurations. In a parallel configuration, the two heterodimer-subunit peptide helixes are aligned such that they have the same orientation (amino-terminal to carboxyl-terminal). In an antiparallel configuration, the helixes are arranged such that the amino-terminal end of one helix is aligned with the carboxyl-terminal end of the other helix, and vice versa. Such heterodimer subunits are described in PCT patent application WO 95/31480 "Heterodimer Polypeptide Immunogen Carrier Composition and Method", publication date 23 Nov. 1995, which is incorporated herein by reference in its entirety. Exemplary subunits are referred to herein as K-coils, referring to positively charged subunits whose charge is provided dominantly by lysine residues, and E-coils, referring to negatively charged subunits whose charge is provided dominantly by glutamic acid residues. Preferred examples from the above-mentioned application include SEQ ID NOS: 1–2.

Heterodimer-subunit peptides designed in accordance with the guidance presented in the above-referenced application typically show a preference for assembling in a parallel orientation versus an antiparallel orientation. For example, the exemplary peptides identified by SEQ ID NO:3 and SEQ ID NO:4 form parallel-configuration heterodimers, as do other peptide sequences (as discussed in the WO 95/31480 application). An additional exemplary peptide includes a K-coil peptide made of 7-amino acid, e.g., SEQ ID NO: 5 repeats. In one embodiment, the K-coil is 35 amino acids in length; it is positively charged, with no specific structure in solution. The E-coil may be a peptide made of 7-amino acid, e.g., SEQ ID NO: 6 repeats. In one embodiment, the E-coil is 35 amino acids in length; it is negatively charged, and has no specific structure in solution.

As noted, one of the two subunit peptides in the heterodimer contains a targeting moiety, and the other peptide contains an active agent. In both cases, the peptide can be synthesized or derivatized after synthesis, to provide the requisite attachment function. An exemplary method of peptide synthesis is described in Example 1. In general, most conjugating methods do not disrupt the coil-forming activity of either of the coil-forming peptide, nor do such conjugations disrupt the activity of the conjugated active agent or targeting moiety.

Considering the modification of the first coil-forming peptide, the peptide may be synthesized at either its N- or C-terminus to carry additional terminal peptides that can function as a spacer between the targeting moiety and the helical-forming part of the peptide. The targeting moiety-coil forming peptide and/or the active agent-coil forming peptide may be synthesized, as noted above, by either solid-state, PCR, or recombinant methods, in vivo or in vitro.

In forming the conjugate through solid-state methods, the active agent or targeting moiety is preferably covalently attached to the N-terminal amino acid residue, or to one of the residues facing the exposed face of the heterodimer. Preferred coupling groups are the thiol groups of cysteine residues, which are easily modified by standard methods. Other useful coupling groups include the thioester of methionine, the imidazolyl group of histidine, the guanidinyl group of arginine, the phenolic group of tyrosine and the indolyl group of tryptophan. These coupling groups can be derivatized using reaction conditions known to those skilled in the art.

To bind the active agent second coil-forming peptide to the targeting moiety-first coil-forming peptide, the two peptides are contacted under conditions that favor heterodimer formation. An exemplary medium favoring coiled-coil heterodimer formation is a physiologically-compatible aqueous solution typically having a pH of between about 6 and about 8 and a salt concentration of between about 50 mM and about 500 mM. Preferably, the salt concentration is between about 100 mM and about 200 mM. An exemplary medium has the following composition: 50 mM potassium phosphate, 100 mM KCl, pH 7. Equally effective media may be made by substituting, for example, sodium phosphate for potassium phosphate and/or NaCl for KCl. Heterodimers may form under conditions outside the above pH and salt range, medium, but some of the molecular interactions and relative stability of heterodimers vs. homodimers may differ from characteristics detailed above. For example, ionic interactions between the ionic groups that tend to stabilize heterodimers may break down at low or high pH values due to the protonation of, for example, Glu side chains at acidic pH, or the deprotonation of, for example, Lys side chains at basic pH. Such effects of low and high pH values on coiled-coil heterodimer formation may be overcome, however, by increasing salt concentration.

Increasing the salt concentration can neutralize the stabilizing ionic attractions or suppress the destabilizing ionic repulsions. Certain salts have greater efficacy at neutralizing the ionic interactions. For example, in the case of the K-coil peptide, a 1 M or greater concentration of $ClO^{4-}$ anions is required to induce maximal α-helical structure, whereas a 3M or greater concentration of $Cl^-$ ions is required for the same effect. The effects of high salt on coiled-coil formation at low and high pH also show that interhelical ionic attractions are not essential for helix formation, but rather, control whether a coiled-coil tends to form as a heterodimer versus a homodimer. The first coil-forming peptide, e.g., an E-coil peptide, and the second coil-forming peptide, e.g., a K-coil peptide can also be conjugated to targeting moieties and active agents as described in Example 2 of co-owned U.S. application Ser. No. 09/654,191 (Attorney Docket #: 4800-0015.31), which is expressly incorporated by reference herein in its entirety. See, also, U.S. Pat. No. 6,300,141, which is incorporated by reference herein in its entirety.

In one embodiment of the invention, the active agent-coil-forming peptide has a short serum half life and is excreted via the renal pathway. Thus, the active agent either accretes to the target site or it is rapidly removed from the subject. This biodistribution of active agent facilitates the protection of normal tissues of the recipient from undesired exposure. In order to enhance renal excretion, conjugation to a renal excretion promoting biodistribution directing molecule may be employed. An alternative to the optional clearance step is to allow a sufficient amount of time to pass which permits the subject's native clearance mechanisms to substantially remove the circulating first conjugate.

In another embodiment, antibody-based or non-antibody-based targeting moieties are employed to deliver a ligand or an anti-ligand to a target site bearing an unregulated antigen. Preferably, a natural binding agent for such an unregulated antigen is used for this purpose. For example, diseases such as hepatoma or myeloma are generally characterized by unregulated IL-6 receptors for which IL-6 acts as an autocrine or paracrine moiety with respect to rapid proliferation of these target cell types. For the treatment of such ailments, IL-6 may therefore be employed as a targeting moiety. See, e.g., Miki, C. et al. (2002) *Cancer* 94(5):1584–92.

For example, IL-6 and a first coil-forming peptide may be conjugated via chemical means or be formed as a recombinant molecule. The IL-6-first coil-forming peptide conjugate is administered to a recipient, and the IL-6 component of the conjugate directs the localization of the conjugate to IL-6 receptors. This localization will occur preferentially to sites bearing unregulated IL-6 receptors. After target site localization occurs, a clearing agent, as described below, is optionally administered to substantially clear the recipient's circulation of IL-6-first coil-forming peptide conjugate. Suitable clearing agents for this purpose are, e.g., IL-6 receptor-HSA-galactose or anti-IL-6-antibody-HSA-galactose. After a time sufficient for substantial, e.g., 50%, 70%, or preferably 90%, clearance of IL-6 from the recipient's circulation, active agent-second coil-forming peptide, e.g., urease-second coil-forming peptide, is administered and localizes to target sites via the IL-6-first coil-forming peptide conjugate.

As described in more detail in Section VII below, expression vectors derived from retroviruses, adenovirus, herpes, or vaccinia viruses, or from various bacterial plasmids, may be used for delivery of recombinant urease molecules to the targeted cell population. Methods that are well known to those skilled in the art can be used to construct recombinant vectors containing urease. See, for example, the techniques described in Sambrook et al., and Ausubel et al. Alternatively, active agents can be delivered to target cells utilizing liposomes or nanocapsules as described in Section II above. In one embodiment, the method of the invention includes adding to the subject a composition containing the active agent and a targeting moiety effective to target the composition to the cells.

C. Clearing Agents

As discussed above, a clearing agent may be administered to a subject. The clearing agent is capable of directing circulating first conjugate to hepatocyte receptors, thereby decreasing the amount of circulating first conjugate prior to administering the second conjugate.

As noted above, clearing agents of protein or nonprotein composition having physical properties facilitating use for in vivo complexation and blood clearance of unbound targeting moiety conjugates may be useful when the tumor cells are contained within a subject, e.g., a human. Clearing agents preferably exhibit one or more of the following characteristics: rapid, efficient complexation with targeting moiety in vivo; rapid clearance from the blood of targeting moiety conjugates capable of binding a subsequently administered active agent; high capacity for clearing or inactivating large amounts of targeting moiety conjugates; and low immunogenicity.

Useful clearing agents include hexose-based and non-hexose based moieties. Hexose-based clearing agents are molecules that have derivatized to incorporate one or more hexoses (six carbon sugar moieties) recognized by Ashwell receptors or other receptors such as the mannose/N-acetylglucosamine receptor which are associated with endothelial cells and/or Kupffer cells of the liver or the mannose 6-phosphate receptor. Exemplary hexoses include galactose, mannose, mannose 6-phosphate, N-acetylglucosamine and the like. Other moieties recognized by Ashwell receptors, including glucose, N-galactosamine, N-acetylgalactosamine, thioglycosides of galactose and, generally, D-galactosides and glucosides may also be used. Galactose thioglycoside conjugation to a protein may be accomplished, e.g., as described in Lee et al. (1976) *Biochemistry*, 15(18): 3956 or Drantz et al., (1976) *Biochemistry*, 15(18):3963.

Protein-type galactose-based clearing agents include proteins having endogenous exposed galactose residues or which have been derivatized to expose or incorporate such galactose residues. Exposed galactose residues direct the clearing agent to rapid clearance by endocytosis into the liver through specific receptors (Ashwell receptors). These receptors bind the clearing agent and induce endocytosis into the hepatocyte, leading to fusion with a lysosome and recycle of the receptor back to the cell surface. This clearance mechanism is characterized by high efficiency, high capacity and rapid kinetics.

An exemplary clearing agent of the protein-based/galactose-bearing variety is the asialoorosomucoid derivative of human alpha-1 acid glycoprotein. The rapid clearance from the blood of asialoorosomucoid is described in Galli, et al., *J of Nucl Med Allied Sci* (1988) 32(2):110–16. Treatment of orosomucoid with neuramimidase removes sialic acid residues, thereby exposing galactose residues. Additional derivatized clearing agents include, e.g., galactosylated albumin, galactosylated-IgM, galactosylated-IgG, asialo-haptoglobin, asialofetuin, and asialoceruloplasmin.

Additional clearing agents are described in U.S. Pat. No. 6,358,490, issued Mar. 19, 2002; U.S. Pat. No. 6,172,045, issued Jan. 9, 2001; and U.S. Pat. No. 5,886,143, issued Mar. 23, 1999, each of which is incorporated by reference herein.

A further class of clearing agents useful in the present invention include small molecules, e.g., ranging from about 500 to about 10,000 Daltons. The small molecules may be derivatized with galactose. The small molecule clearing agents are preferably capable of (1) rapidly and efficiently complexing with the relevant conjugate, coil-forming peptide, active agent, and/or targeting moiety; and (2) clearing such complexes from the blood via the galactose receptor, a liver specific degradation system, as opposed to aggregating into complexes that are taken up by, e.g., the lung and spleen. Additionally, the rapid kinetics of galactose-mediated liver uptake, coupled with the affinity of the ligand-anti-ligand interaction, allow the use of intermediate or even low molecular weight carriers.

In one embodiment of the invention, protein-type and polymer-type non-galactose-based clearing agents are used. These clearing agents may act through an aggregation-mediated mechanism. In this embodiment of the invention, the clearing agent used may be selected based on the target organ to which access of the clearing agent is to be excluded.

For example, high molecular weight, e.g., ranging from about 200,000 to about 1,000,000 Daltons may be useful when tumor cell targets are involved.

Another class of clearing agents includes agents that do not remove circulating active agent/targeting moiety conjugates, but instead inactivate the circulating conjugates by blocking the relevant sites on the active agent, targeting moiety, liposome, viral vector, and/or any other portion thereof. These "cap-type" clearing agents are preferably small, e.g., 500 to 10,000 Daltons, highly charged molecules, e.g., derivatized 6,6'-[(3,3'-dimethyl[1,1'-biphenyl]-4,4'-diyl)bis(azo)bis[4-amino-5-hydroxy-1,3-naphthalene disulfonic acid] tetrasodium salt.

E. Dosage/Administration

For the method of the invention, any effective administration regimen regulating the timing and sequence of doses may be used. Exemplary dosage levels for a human subject will depend on the mode of administration, extent (size and distribution) of the tumor, patient size, and responsiveness of the cancer to urease treatment.

Where a urease composition is injected directly into a tumor, an exemplary dose is 0.1 to 1,000 international units urease activity per $mm^3$ tumor. For example, and assuming a relatively uniform distribution of the urease in the tumor is achieved, a dose of between 0.5 and 5 international units may be suitable. The placement of the injection needle may be guided by conventional image guidance techniques, e.g., fluoroscopy, so that the physician can view the position of the needle with respect to the target tissue. Such guidance tools can include ultrasound, fluoroscopy, CT or MRI.

In accordance with one aspect of the invention, the effectiveness or distribution of the administered urease dose may be monitored, during or after direct injection of urease into the tumor, by monitoring the tumor tissue by a tool capable of detecting changes in pH within the cancerous tissue region of the subject. Such tools may include a pH probe that can be inserted directly into the tumor, or a visualization tool, such as magnetic resonance imaging (MRI), computerized tomography (CT), or fluoroscopy. MRI interrogation may be carried out in the absence of additional imaging agents, based simply on differences in magnetic properties of tissue as a function of pH. CT or fluoroscopic imaging may require an additional pH-sensitive imaging agent whose opacity is affected by the pH of the tissue medium. Such agents are well known to those of skill in the art.

Before any urease injection, the tumor tissue can be visualized by its lower pH relative to surrounding normal tissue. Thus, the normal tissue may have a normal pH of about 7.2, whereas the tumor tissue may be 0.1 to 0.4 or more pH units lower. That is, before any urease is injected, the extent of tumor tissue can be defined by its lower pH. Following urease administration, the pH of the tumor region having urease will begin to rise, and can be identified by comparing the resulting images with the earlier pre-dosing images.

By interrogating the tissue in this manner, the degree of change in pH and extent of tissue affected may be monitored. Based on this interrogation, the physician may administer additional composition to the site, and/or may administer composition at additional areas within the tumor site. This procedure may be repeated until a desired degree of pH changes, e.g., 0.2 to 0.4 pH units, has been achieved over the entire region of solid tumor.

Dosing by direct injection may be repeated by suitable intervals, e.g., every week or twice weekly, until a desired end point, preferably substantial or complete regression of tumor mass is observed. The treatment efficacy can be monitored, as above, by visualizing changes in the pH of the treated tissue during the course of treatment. Thus, before each additional injection, the pH of the tissue can be visualized to determine the present existing extent of tumor, after which changes in the pH of the tissue can be used to monitor the administration of the new dose of urease composition to the tissue.

Where the urease is administered parenterally by a method other than direct injection, an exemplary dose of the urease is 100–100,000 international units/kg urease activity/kg subject body weight. As noted herein, the urease composition in this method preferably includes a targeting agent for targeting urease to the cancer cells, e.g., site of solid tumor, or for sequestering urease, e.g., in liposomal form, selectively at the tumor site.

As above, imaging techniques that are sensitive to changes in tissue pH, may be used to monitor the effectiveness of the dose administered. Since such targeting may take several hours or more, the method may involve monitoring tumor pH, as above, before urease injection, and several hours, e.g., 12–24 hours following dosing, to confirm that the tumor site has been adequately dosed, as evidenced by rise in pH of the tumor region. Depending on the results of this interrogation, the method may dictate additional dosing until a desired rise in pH, e.g., 0.2–0.4 pH units, is observed. Once this dose is established, the patient may be treated with a similar dose of the urease composition on a regular basis, e.g., one or twice weekly, until a change in tumor size or condition is achieved.

In both types of administration, final dosage regimen will be determined by the attending physician in view of good medical practice, considering various factors that modify the action of drugs, e.g., the agent's specific activity, the severity of the disease state, the responsiveness of the patient, the age, condition, body weight, sex, and diet of the patient, the severity of any infection, and the like. Additional factors that may be taken into account include time and frequency of administration, drug combination(s), reaction sensitivities, and tolerance/response to therapy. Further refinement of the dosage appropriate for treatment involving any of the formulations mentioned herein is done routinely by the skilled practitioner, especially in light of the dosage information and assays disclosed, as well as the pharmacokinetic data observed in clinical trials. Appropriate dosages may be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active agent or to maintain the desired effect. Accordingly, the pharmaceutical compositions can be administered in a single dose, multiple discrete doses, continuous infusion, sustained release depots, or combinations thereof, as required to maintain desired minimum level of the agent.

Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, may be preferred for continuous infusion.

Compositions comprising an active agent of the invention formulated as described in Section II, above, in a pharmaceutical acceptable carrier may be prepared, placed in an appropriate container, and labeled for treatment of an indicated condition. Conditions indicated on the label may include, but are not limited to, treatment and diagnosis of various cancer types. Kits, as described below, are also contemplated, wherein the kit comprises a dosage form of a pharmaceutical composition and a package insert containing instructions for use of the composition in treatment of a medical condition.

Generally, the active agents used in the invention are administered to a subject in an effective amount. Generally, an effective amount is an amount effective to either (1) reduce the symptoms of the disease sought to be treated; or (2) induce a pharmacological change relevant to treating the disease sought to be treated. For cancer, an effective amount may include an amount effective to: reduce the size of a tumor; slow the growth of a tumor; prevent or inhibit metastases; or increase the life expectancy of the affected subject. An exemplary method of administering the active agent to mice is described in Example 6, below.

Active agents, clearing agents, and/or imaging agents of the present invention may be administered in single or multiple doses. Alternatively, the agents may be infused intravenously over an extended period of time. For example, a clearing agent may be administered intravenously for a time period sufficient to clear the targeting moiety in a continuous manner.

In the multi-targeting moiety administering embodiments of the invention, described above, the doses of each administered component may be determined by the attending physician in accordance with his or her experience; the particulars of the recipient's condition, e.g., the nature and location of the target site, including the antigens associated therewith, will impact target moiety selection and route of administration decisions; and the combination of targeting moiety to be employed, e.g., antibody performance may vary with respect to antigen density and the affinity of the antibody for the antigen.

IV. Method of Potentiating an Anticancer Drug

As noted above, one of the limitations in current chemotherapy is that the target tumor becomes increasingly resistant to the effect of the anti-tumor compound. This resistance may be due to reduced uptake of the compound into tumor cells, reduced availability of the drug at the site of uptake, or increased intracellular metabolism.

For a number of weakly basic drugs, that is, drugs having one or more protonizable amines, the mechanism of drug uptake may involve passive diffusion across the cell membrane in uncharged form. Accordingly, the rate of movement of the compound across the cell membrane will depend on the inside/outside pH gradient. If the extracellular pH is equal to or greater than the intracellular pH, e.g., around pH 7.2, the compound will tend to pass into the cells in uncharged form at least as frequently as it exits the cell. Conversely, as the extracellular pH falls with respect to intracellular pH, as it does in solid tumors, the lower outside pH will favor the charged, protonated form of the compound, and this will inhibit uptake of the drug into the cells. In effect, one of the effects of the lower extracellular pH in tumors is to protect the tumor against weakly basis anti-tumor compounds.

Weakly basic anti-tumor compound whose activity can be adversely affected by a lower extracellular pH include doxorubicin, daunorubicin, mitoxanthrone, epirubicin, mitomycin, bleomycin, vinca alkaloids such as vinblastine and vincristine, alkylating agents such as cyclophosphamide and mechlorethamine hydrochloride, and antrineoplastic purine and pyrimidine derivatives.

In the present method, urease or a urease containing composition is administered to a solid tumor in an amount effective to raise the extracellular pH of the tumor fluid at least 0.1 pH unit, e.g., 0.1 to 0.5 pH units or more. In certain embodiments, the extracellular pH of the fluid is raised to at least pH 7.0, 7.2, or higher.

The urease may be administered as described in Section III above, e.g., directly into the subject's tumor or parenterally other than by direct injection. Also as described above, the change in pH produced by the administration of urease may be monitored by determining changes in pH in tumor tissue and the extent of those changes, using imaging tools for visualizing tumor pH, or by direct pH measurements of the tumor.

The dose administered in this method may be less than that needed where urease is the sole anti-tumor agent, as long as the amount injected is sufficient to produce the desired rise in tumor pH. Alternatively, the method may involve administration of a therapeutic amount of urease and a therapeutic or subtherapeutic amount of the anti-cancer compound. As can be appreciated, the method may allow a lower than normal dose of the anti-tumor compound to be given, both because urease enhances therapeutic effect of the compound, and because urease is itself contributing to the therapeutic effect. Greater efficacy with fewer side effects result.

In one embodiment, a chemical entity, as described above, may also be associated with the active agent to enhance the delivery of the active agent. In this embodiment, the active agent may be administered by any method, e.g., parenterally, other than direct injection.

V. Method of Monitoring Anticancer Treatment

The invention also provides, in yet another aspect, a method of monitoring anticancer treatment by assessing the presence, size or condition a solid tumor in a subject. The method includes administering an active agent as described above, e.g., urease, to a subject that contains, or is suspected of containing, a solid tumor. The active agent is administered under conditions effective to localize the active agent in the solid tumor in the subject.

The subject is interrogated with a diagnostic tool capable of detecting changes in extracellular pH in a subject's tissue, as described above. The diagnostic tool is preferably a pH-sensitive diagnostic agent, such as an imaging, contrast or shift reagent, as described in Section II, above, capable of localizing in the tumor that may be administered prior to, following or concurrently with the active agent. A tissue region is identified within the subject that shows an elevation in extracellular pH following the administration. Any tool capable of identifying the diagnostic agent may be used to detect the agent, such as MRI, PET scan, and the like as described above.

In one embodiment, the method includes administering urease to the subject employed in an anti-tumor therapy, and the identification is used for detecting the localization of urease in a solid tumor.

The identifying may be used for monitoring the change in size and shape of the tumor in response to urease administration.

In one embodiment employing PET scan, the subject is administered 13N-labelled ammonia. The patient is then administered urease in an amount effective to reach the tumor site. The urease hydrolyzes urea to produce nonlabelled ammonia. Over time, the labelled ammonia is diluted or displaced, causing a gradual clearing on the scan.

In another embodiment employing PET scan, the subject is administered 13N-labelled urea. The patient is then administered urease in an amount effective to reach the tumor site. The urease hydrolyzes the labelled urea to produce labelled ammonia, which could be detected on the scan.

VI. Kits

In still another aspect, this invention provides kits for inhibiting the growth of tumor cells using the methods described herein. The kits include a container containing one or more active agents. The kits can additionally include any of the other components described herein for the practice of the methods of this invention. Such components include, but are not limited to pharmaceutical components, targeting moieties, imaging agents, clearing agents, gene therapy components, and the like.

The kits may optionally include instructional materials containing directions (i.e., protocols) disclosing the use of active agents for inhibiting tumor cell growth. Thus, in one embodiment, the kit includes a pharmaceutical composition containing an active agent, preferably a urease enzyme, and instructional materials teaching the administration of the composition to a subject, for the treatment of a cancer in the subject. In one embodiment, the instructional material teaches administering the urease composition to a subject in an amount which is dependent on the size of the tumor and between 0.1 to 100 international units urease activity per $mm^3$ tumor, when the composition is administered by direct injection into the tumor, and in an amount between 100–100,000 international units/kg international units urease activity/kg subject body weight, when the composition is administered parenterally to the subject other than by direct injection into the tumor.

In another embodiment, the instructional material teaches administering the urease composition to a subject who is also receiving a weakly basic anti-tumor compound whose effectiveness is reduced by a higher intracellular/lower extracellular pH gradient in a solid tumor, in an amount of urease effective to reduce or reverse the higher intracellular/lower extracellular pH gradient in a solid tumor.

Alternatively, the instructional material teaches administering the urease composition to a subject containing, or suspected of containing, a solid tumor, under conditions effective to localize the urease in a solid tumor in the subject, interrogating the subject with a diagnostic tool capable of detecting changes in extracellular pH in a subject's tissue, and identifying a tissue region within the subject that shows an elevation in extracellular pH following said administering.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

VII. Gene/Cell Therapy

A gene therapy composition is also contemplated, in another aspect of the invention, for use in inhibiting growth of cancer cells in a mammalian subject. The gene therapy composition includes a targeting vector effective, when administered to the subject, of selectively transfecting cancer cells, and carried in said vector, a recombinant nucleic acid sequence effective to produce a nucleic acid molecule, e.g., mRNA, which encodes the active agent, preferably urease, in transfected cancer cells.

In one embodiment, the tumor cells are contacted with engineered non-tumorigenic cells that express a heterologous nucleic acid molecule that encodes the active agent. The non-tumorigenic engineered cells may be, without limitation, fibroblasts, epithelial cells, endothelial cells, bone cells, keratinocytes, or irradiated, engineered non-tumorigenic cells derived from tumors.

In another embodiment, the tumor cells are transfected with a gene construct encoding a cell targeting moiety and a heterologous nucleic acid molecule which encodes the urease protein and a secretory leader sequence. The gene construct is capable of expressing the cell targeting moiety and heterologous urease protein and the secretory leader sequence as a conjugate within the tumor cells and whereby the conjugate is directed by the secretory leader sequence to leave the cell thereafter for selective localization at a cell surface antigen recognized by the cell targeting moiety.

Preferably, the cell targeting moiety is selectively localized to a cell surface antigen, and the cell surface antigen is specific for at least one human solid tumor. The gene construct may comprise a transcriptional regulatory sequence comprising a promoter and a control element which comprises a genetic switch to control expression of the gene construct.

According to one embodiment of the invention, the gene construct is packaged within a viral vector. A variety of viral vectors are available for tumor targeting. Parvivirus are known to infect tumor cells selectively. Alternatively, the virus can be designed to replicate selectively in tumor cells, according to published methods. See, for example, Puhlmann M; et al., *Hum Gene Ther*, (1999) 10 (4):649–57; Noguiez-Hellin P; et al. *Proc Natl Acad Sci USA*, (1996) 93(9):4175–80; and Cooper M J, *Semin Oncol* (1996) 23(1) 172–87. For example, the virus may be altered to contain a mutated thymidine kinase or polymerase gene that allows viral replication only in rapidly dividing cells containing these enzymes. Alternatively, the virus can be genetically engineered to contain tumor-specific control elements, e.g., tumor-specific promoter regions, that are responsive and express the desired protein or protein necessary for viral replication only in tumor cells. Preferably, the gene construct is packaged within an adenovirus.

A. Vectors for Cloning, Gene Transfer and Expression

Within certain embodiments of the invention, expression vectors are employed to express the urease polypeptide product, which may then be purified. In other embodiments, the expression vectors are used in gene therapy. Expression vectors may include appropriate signals be provided in the vector, and various regulatory elements, such as enhancers/promoters from viral and/or mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

B. Regulatory Elements

The term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. The promoters may be composed of discrete functional modules, each consisting of approximately 7–20 bp of DNA, and containing one or more recognition sites for transcriptional activator or repressor proteins. At least one module in each promoter functions to position the start site for RNA synthesis. An exemplary module is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally, such a promoter may include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase may be used to obtain high-level expression of the coding sequence of interest. The use of other viral or mammalian cellular or bacterial phage promoters, which are well-known in the art to achieve expression of a coding sequence of interest, is contemplated as well.

Where a cDNA insert is employed, one may desire to include a polyadenylation signal to effect proper polyadenylation of the gene transcript. The nature of the polyadenylation signal is not believed to be crucial to the successful practice of the invention, and any such sequence may be employed, such as human growth hormone and SV40 polyadenylation signals. Also contemplated as an element of the expression cassette is a terminator. These elements can serve to enhance message levels and to minimize read through from the cassette into other sequences.

C. Selectable Markers

In certain embodiments of the invention, the cells containing nucleic acid constructs of the present invention may be identified in vitro or in vivo by including a marker in the expression construct. Such markers confer an identifiable change to the cell permitting easy identification of cells containing the expression construct. Typically, the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase may be employed. Immunologic markers also may be employed. Further examples of selectable markers are well known to one of skill in the art. See, e.g., Baumann, R. P. et al. (2002) *Biotechniques* 32(5):1030–34.

D. Delivery of Expression Vectors

There are a number of ways in which expression vectors may be introduced into cells. In certain embodiments of the invention, the expression construct comprises a virus or engineered construct derived from a viral genome which is used to deliver a urease composition to a target cell. The ability of certain viruses to enter cells via receptor-mediated endocytosis, to integrate into host cell genome, and express viral genes stably and efficiently, have made them attractive candidates for the transfer of foreign genes into mammalian cells.

One of the preferred methods for in vivo delivery involves the use of an adenovirus expression vector. "Adenovirus expression vector" is meant to include those constructs containing adenovirus sequences sufficient to (a) support packaging of the construct and (b) to express a polynucleotide that has been cloned therein. In this context, expression does not require that the gene product be synthesized. See, e.g., Barnett, B. G., et al. (2002) "Targeted Adenovirus Vectors" *Biochim Biophys Acta* 1575(1–3):1–14.

In one embodiment of the invention, the expression vector may comprise a genetically engineered form of adenovirus. Knowledge of the genetic organization of adenovirus, a 36 kb, linear, double-stranded DNA virus, allows substitution of large pieces of adenoviral DNA with foreign sequences up to 7 kb. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target cell range and high infectivity. Generation and propagation of adenovirus vectors may depend on a helper cell line. Helper cell lines may be derived from human cells, such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. An exemplary helper cell line is the 293 cell line, which was transformed from human embryonic kidney cells by Ad5 DNA fragments and constitutively expresses E1 proteins. Methods for culturing 293 cells and propagating adenovirus have been described.

Additional viral vectors may be employed as expression constructs in the present invention. Vectors derived from viruses such as vaccinia virus (Walther, W. and Stein, U. (2000) *Drugs* 60(2):249–71), adeno-associated virus (Zhao, N. et al. (2001) *Mol Biotechnol* 19(3):229–37) and herpesviruses (Burton, E. A. et al. (2001) *Adv Drug Deliv Rev* 53(2):155–70) may be employed. Additional tumor-specific, replication-selective viruses that may be used in the present invention are reviewed in Hawkins, L. K. et al. (2002) *Lancet Oncol* 3(1):17–26.

Several non-viral methods for the transfer of expression constructs into cultured mammalian cells also are contemplated by the present invention. These include calcium phosphate precipitation, DEAE-dextran, electroporation, direct microinjection, DNA-loaded liposomes and lipofectamine-DNA complexes, cell sonication, gene bombardment using high velocity microprojectiles, and receptor-mediated transfection.

Once the expression construct has been delivered into the cell, the nucleic acid encoding the gene of interest, e.g., the urease gene, may be positioned and expressed at different sites. In certain embodiments, the nucleic acid encoding the active agent may be stably integrated into the genome of the cell. This integration may be in the cognate location and orientation, via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. The method of delivery of the expression construct and the location in the cell where the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro, but it may be applied to in vivo use as well.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them. Several devices for accelerating small particles are useful in this regard. One such device relies on a high voltage discharge to generate an electrical current, which in turn provides the motive force. The microprojectiles used may consist of biologically inert substances such as tungsten or gold beads.

In one embodiment, such expression constructs may be entrapped in a liposome, lipid complex, nanocapsule, or other formulation using one or more of the methods disclosed in Section II, above. Also contemplated are lipofectamine-DNA complexes.

In certain embodiments of the invention, the liposome may be complexed with a hemagglutinating virus (HVJ). In other embodiments, the liposome may be complexed or employed in conjunction with nuclear non-histone chromosomal proteins (HMG-1). In yet further embodiments, the liposome may be complexed or employed in conjunction with both HVJ and HMG-1.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific.

Receptor-mediated gene targeting vehicles generally consist of two components: a cell receptor-specific ligand and a DNA-binding agent. Several ligands have been used for receptor-mediated gene transfer, e.g., asialoorosomucoid and transferrin. In addition, epidermal growth factor (EGF) has also been used to deliver genes to squamous carcinoma cells (Eur. Pat. Appl. Publ. No. EP 0360257, specifically incorporated herein by reference).

In other embodiments, the delivery vehicle may comprise a ligand and a liposome. Thus, it is feasible that a nucleic acid encoding a particular gene also may be specifically delivered into a cell type such as lung, epithelial or tumor cells, by any number of receptor-ligand systems with or without liposomes. For example, EGF or other small molecules may be used as the receptor for mediated delivery of a nucleic acid encoding a gene in many tumor cells that exhibit upregulation of EGF receptor (Basela, J. (2002) *J Clin Oncol* 20(9):2217–9). Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues. See, e.g., Ahonen, M. et al. (2002) *Mol Ther* 5(6):705–15 and Kawai, K. et al. (2000) *Mol Urol* 4(2):43–6; U.S. Pat. Nos. 6,395,712, 6,149,904, and 6,410,029, each of which is incorporated herein by reference.

Primary mammalian cell cultures may be prepared in various ways. In order for the cells to be kept viable while in vitro and in contact with the expression construct, the cells typically will maintain contact with the correct ratio of oxygen and carbon dioxide and nutrients and be protected from microbial contamination. Cell culture techniques are well known to those of skill in the art.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for gpt, that confers resistance to mycophenolic acid; neo, that confers resistance to the aminoglycoside G418; and hygro, that confers resistance to hygromycin.

From the foregoing, it can be seen how various objects and features of the invention are met.

TABLE 2

| Sequences Provided In Support Of The Invention. | |
|---|---|
| Description | SEQ. NO. |
| E-coil:<br>Glu Val Ser Ala Leu Glu Lys Glu Val Ser Ala<br>Leu Glu Lys Glu Val Ser Ala Leu Glu Lys Glu<br>Val Ser Ala Leu Glu Lys Glu Val Ser Ala Leu<br>Glu Lys | 1 |

TABLE 2-continued

Sequences Provided In Support Of The Invention.

| Description | SEQ. NO. |
|---|---|
| K-coil:<br>Lys Val Ser Ala Leu Lys Glu Lys Val Ser Ala<br>Leu Lys Glu Lys Val Ser Ala Leu Lys Glu Lys<br>Val Ser Ala Leu Lys Glu Lys Val Ser Ala Leu<br>Lys Glu | 2 |
| Glu Val Glu Ala Leu Gln Lys Glu Val Ser Ala<br>Leu Glu Lys Glu Val Ser Ala Leu Glu Cys Glu<br>Val Ser Ala Leu Glu Lys Glu Val Glu Ala Leu<br>Gln Lys | 3 |
| Lys Val Glu Ala Leu Lys Lys Lys Val Ser Ala<br>Leu Lys Glu Lys Val Ser Ala Leu Lys Cys Lys<br>Val Ser Ala Leu Lys Glu Lys Val Glu Ala Leu<br>Lys Lys | 4 |
| K-coil:<br>KVSALKE | 5 |
| E-coil:<br>EVSALEK | 6 |
| Jack Bean Urease<br>MKLSPREVEKLGLHNAGYLAQKRLARGVRLNYTEAVALIASQIM<br>EYARDGEKTVAQLMCLGQHLLGRRQVLPAVPHLLNAVQVEATFP<br>DGTKLVTVHDPISRENGELQEALFGSLLPVPSLDKFAETKEDNR<br>IPGEILCEDECLTLNIGRKAVILKVTSKGDRPIQVGSHYHFIEV<br>NPYLTFDRRKAYGMRLNIAAGTAVRFEPGDCKSVTLVSIEGNKV<br>IRGGNAIADGPVNETNLEAAMHAVRSKGFGHEEEKDASEGFTKE<br>DPNCPFNTFIHRKEYANKYGPTTGDKIRLGDTNLLAEIEKDYAL<br>YGDECVFGGGKVIRDGMGQSCGHPPAISLDTVITNAVIIDYTGI<br>IKADIGIKOGLIASIGKAGNPDIMNGVFSNMIIGANTEVIAGEG<br>LIVTAGAIDCHVHYICPQLVYEAISSGITTLVGGGTGPAAGTRA<br>TTCTPSPTQMRLMLQSTDDLPLNFGFTGKGSSSKPDELHEIIKA<br>GAMGLKLHEDWGSTPAAIDNCLTIAEHHDIQINIHTDTLNEAGF<br>VEHSIAAFKGRTIHTYHSEGAGGGHAPDIIKVCGIKNVLPSSTN<br>PTRPLTSNTIDEHLDMLMVCHHLDREIPEDLAFAHSRIRKKTIA<br>AEDVLNDIGAISIISSDSQAMGRVGEVISRTWQTADKMKAQTGP<br>LKCDSSDNDNFRIRRYIAKYTINPAIANGFSQYVGSVEVGKLAD<br>LVMWKPSFFGTKPEMVIKGGMVAWADIGDPNASIPTPEPVKMRP<br>MYGTLGKAGGALSIAFVSKAALDQRVNVLYGLNKRVEAVSNVRK<br>LTKLDMKLNDALPEITVDPESYTVKADGKLLCVSEATTVPLSRN<br>YFLF | 7 |

IV. EXAMPLES

The following examples further illustrate the invention described herein and are in no way intended to limit the scope of the invention.

A. Example 1

A1. Peptide Synthesis

Peptides were prepared by solid-phase synthesis methodology using conventional N-t-butyloxycarbonyl (t-Boc) chemistry. Peptides were cleaved from the resin by reaction with hydrogen fluoride (20 ml/g resin) containing 10% anisole and 2% 1,2-ethanedithiol for 1.5 h at 4° C. Crude peptides were washed with cold ether, and extracted from the resin with glacial acetic acid and freeze-dried. Synthetic peptide was purified by reversed-phase HPLC on a Zorbax semi-preparative C-8 column (250×10 mm I.D., 6.5-μm particle size, 300-Å pore size) with a linear AB gradient (ranging from 0.2 to 1.0% B/min) at a flow rate of 2 ml/min, where solvent A is aqueous 0.05% trifluoroacetic acid (TFA) and solvent B is 0.05% TFA in acetonitrile. Homogeneity of the purified peptides was verified by analytical reversed phased-HPLC, amino acid analysis and MALDI mass spectrometry.

A2. Affinity Purification of Urease

The affinity column was prepared by reacting hydroxyurea to epoxy-activated Sepharose 6B (Amersham Biosciences). Remaining active groups were blocked using 1 M ethanolamine.

Figure 2:
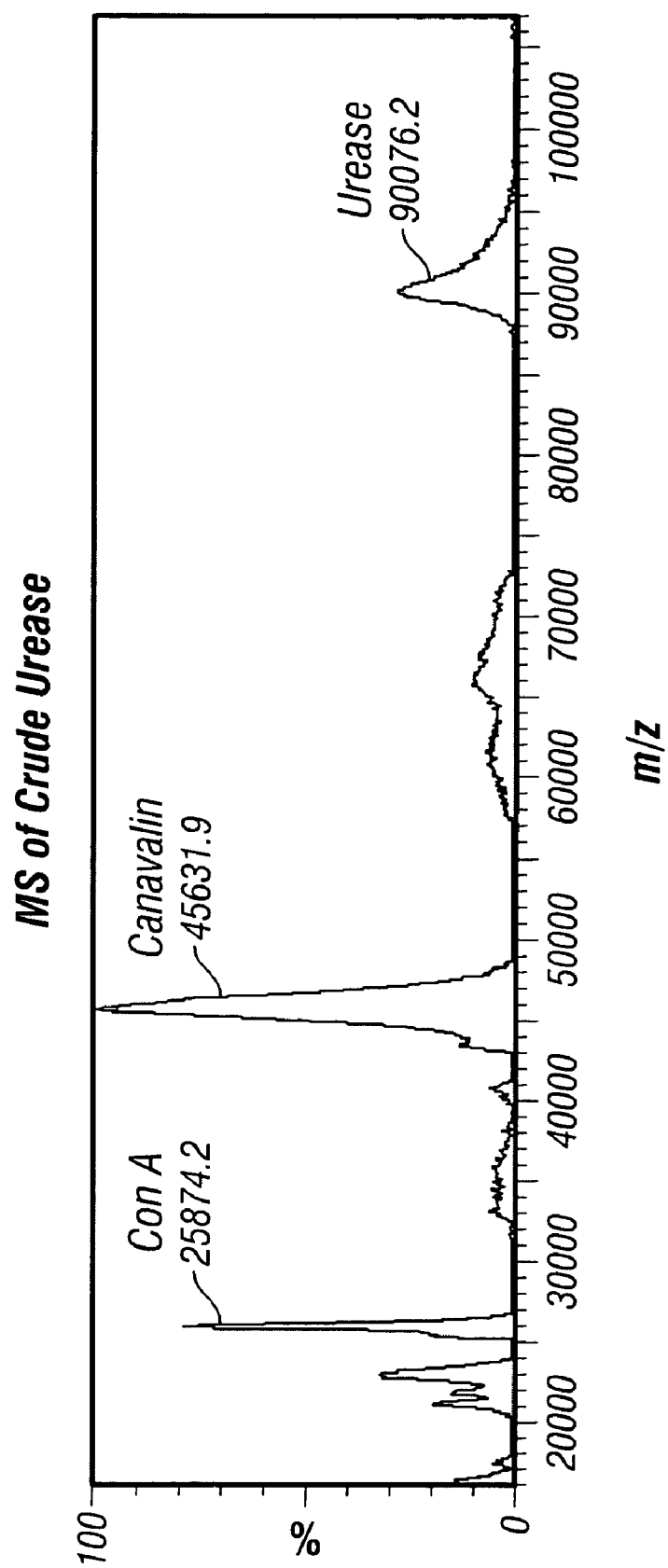
FIG. 2 shows the mass spectrometry profile of a crude sample containing urease prepared in accordance with one embodiment of the invention.
Figure 3A:
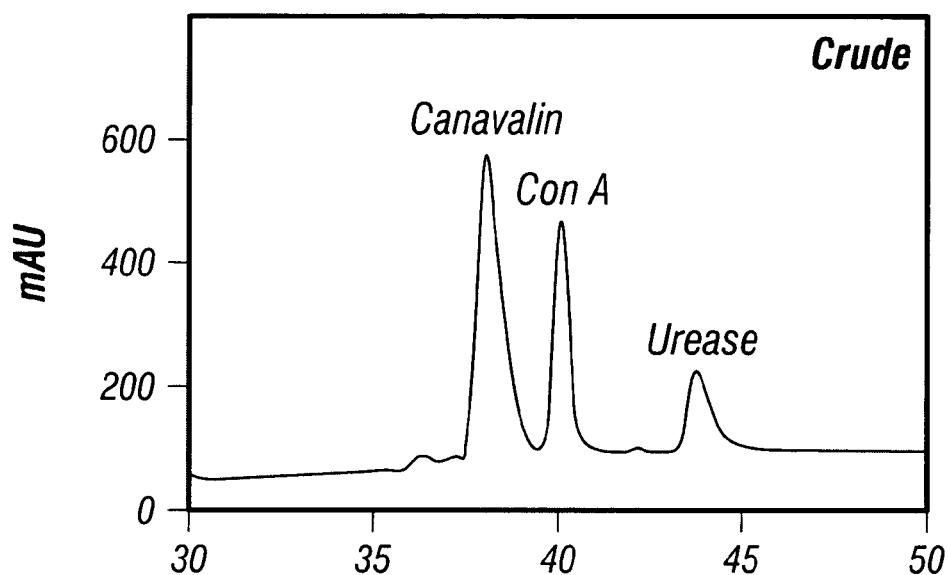
FIG. 3 illustrates the affinity purification profiles of urease during various stages of the purification process, in accordance with another embodiment of the invention.
Figure 3B:
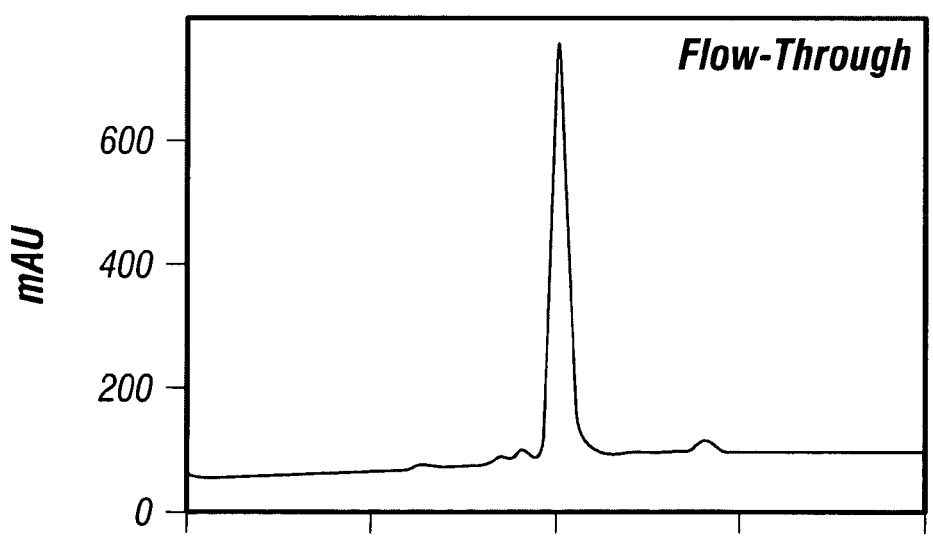
Figure 3C:
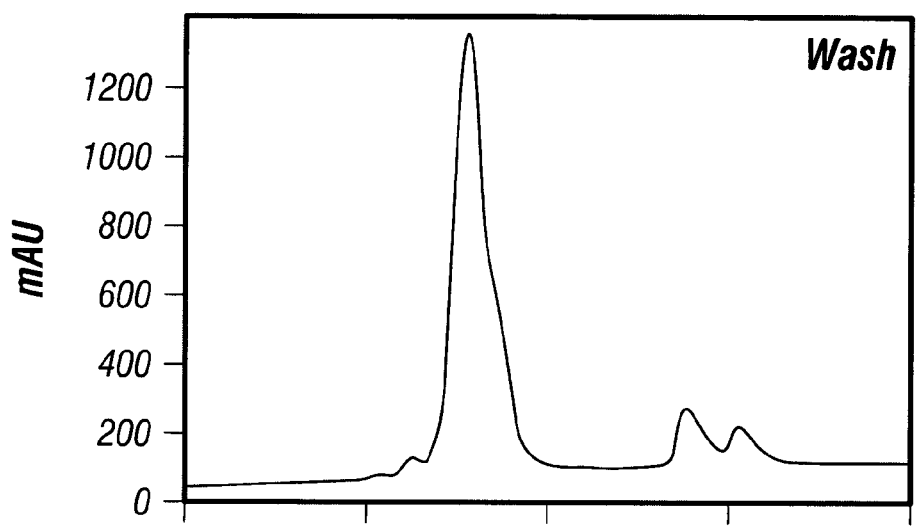
Figure 3D:
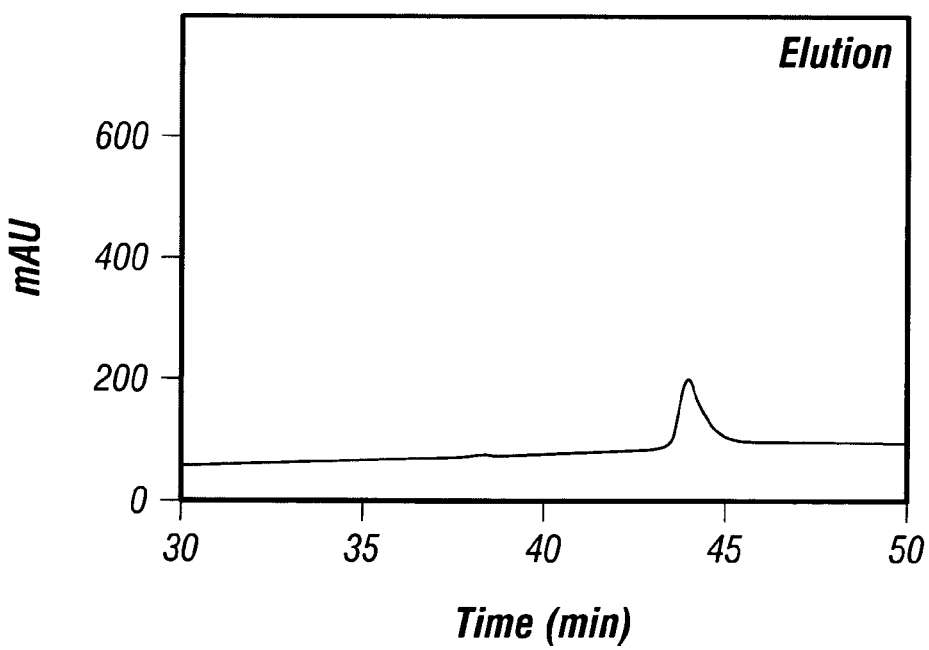

Purification was performed as follows. The column was equilibrated with PEB (0.02 M phosphate, 1 mM EDTA, 1 mM β-mercaptoethanol, pH 7.0). A crude urease sample (FIG. 2) was applied (0.5 mg/ml in PEB, total 8 ml). The column was washed with 15 ml of PB (0.02 M phosphate, 1 mM β-mercaptoethanol, pH 7.0). The column was then washed with 8 ml of each of the following: PB+0.1 M NaCl, PB+0.5 M NaCl, and PB+0.95 M NaCl. The urease was eluted with 8 ml of EB (0.2 M phosphate, 1 mM β-mercaptoethanol, pH 4.6), collecting 1 ml fractions. Fractions were checked by reading OD at 280 nm (FIG. 3) and HPLC (C5 column) analysis. The column was stored in 0.01% NaN$_3$

B. Example 2

Preparation of the Urease-Coil Conjugate

Urease coil conjugate was prepared by dissolving 10 mg of Jack bean Urease in 300 ul of 2 mM phosphate buffer pH 7.2. Then 5 mg of the bifunctional cross-linker Sulfo-MBS was added to the solution and the mixture was slowly stirred for one hour at room temperature. The mixture was then dialyzed against 2 mM phosphate buffer at pH 7.2 to remove excess linker.

K-coil or E-coil with a C-terminal cys linker (1.5 mg) was added to the linker-modified urease solution and slowly mixed for 3 hours at room temperature. The coil urease conjugate was dialyzed against fresh 2 mM phosphate buffer at pH 7.2 overnight to remove unconjugated coil peptide. Dialyzed urease conjugate was lyophilized, then dissolved in 1 mL of 2 mM phosphate buffer pH 7.2 and applied to sephadex G75 column for further purification. The void volume fractions, which contained the coil urease conjugate, were pooled, freeze-dried and stored at 4° C.

The purity of the conjugate and the ratio of the coil to urease in the preparation were determined by amino acid analysis and MALDI mass spectrometry using standard procedures.

C. Example 3

Activity Assay of Urease and Urease Conjugate

The enzymatic activity of urease or urease conjugate was carried out in a coupled enzyme reaction with glutamate dehydrogenase (GLDH). The amount of NADH oxidized was determined by measuring the change in absorbance at 340 nm (Kaltwasser, H. and Schlegel, H. G., Anal. Biochem., 16, 132, 1966). The reagents used were: 0.10 M Potassium phosphate buffer, pH 7.6; 1.80 M Urea prepared in phosphate buffer; 0.025 M Adenosine-5'-diphosphate (ADP) (10.7 mg/ml) in buffer; 0.008 M NADH (5 mg/ml) in phosphate buffer; 0.025 M α-Ketoglutarate (3.7 mg/ml) in phosphate buffer; Glutamate dehydrogenase (GLDH) solution, free from ammonium ions; 50 U/ml phosphate buffer prepared fresh prior to assay. Urease solution was prepared by dissolving in phosphate buffer to yield a concentration of 0.1–0.5 U/ml. This solution was prepared fresh prior to assay.

Assay was initiated by adding the following 2.0 mL of Phosphate buffer 2.40 ml, 0.10 ml each of urea, ADP, NADH, GLDH and α-Ketoglutarate in a cuvette. The spectrophotometer was adjusted to 340 nm and 25° C. The cuvette with the added ingredients was placed in the spectrophotometer at 25° C. for 5 minutes to attain temperature equilibration and then establish blank rate, if any, at 340 nm.

To initiate the enzymatic reaction 0.1 ml of the urease solution was added to the cuvette. The changes in the absorbance at 340 nm were recorded for 15 min. Enzyme activity was correlated with a decrease in absorbance at 340 nm per min.

D. Example 4

Preparation of Coil Antibody Conjugate

Materials include: (1) Rat Anti-hEGFR IgG2a (Serotec), 200 μg/0.2 ml (i.e. 1 mg/ml); (2) E-coil (N-linker); (3) Sodium m-periodate (Pierce); and (4) Bifunctional crosslinker, KMUH (Pierce).

Functional modification of E-coil was performed by performing the following steps:
a. Dissolve KMUH in DMSO to prepare a 10 mg/ml solution (2.5 mg in 250 μl of DMSO).
b. Dissolve E-coil in PB (~2 mg in 392 μl of 10 mM PB, pH 7.4+4 μl of TCEP, 100 mM stock)
c. Add 1 μl of Tris (2 M) to neutralize the E-coil solution
d. Add E-coil solution to the KMUH solution and incubate at R.T. for 2 hr
e. Keep solution at 4° C. overnight
f. Next morning, centrifuge at 12000 rpm for 5 min. to remove insoluble precipitate.
g. Remove KMUH and DMSO on a C8 HPLC column (0–20% acetonitrile/$H_2O$ with 0.05% TFA) and collect all peptide fractions (75% acetonitrile).
g. Lyophilize the peptide fractions and check by MS.

The antibody was oxidized by the following steps:
a. For each 2 mg of antibody, weigh 20 mg of periodate in an amber vial.
b. Add 2 ml of PBS, pH 7.2 and 2 ml of stock antibody to the vial (final [antibody] is 0.5 mg/ml) and gently swirl until the periodate powder was dissolved.
c. Incubate at room temp. for 30 min.
d. Remove periodate by dialyzing 3 times vs 100 mM acetate buffer, pH 5.5.

Figure 4:
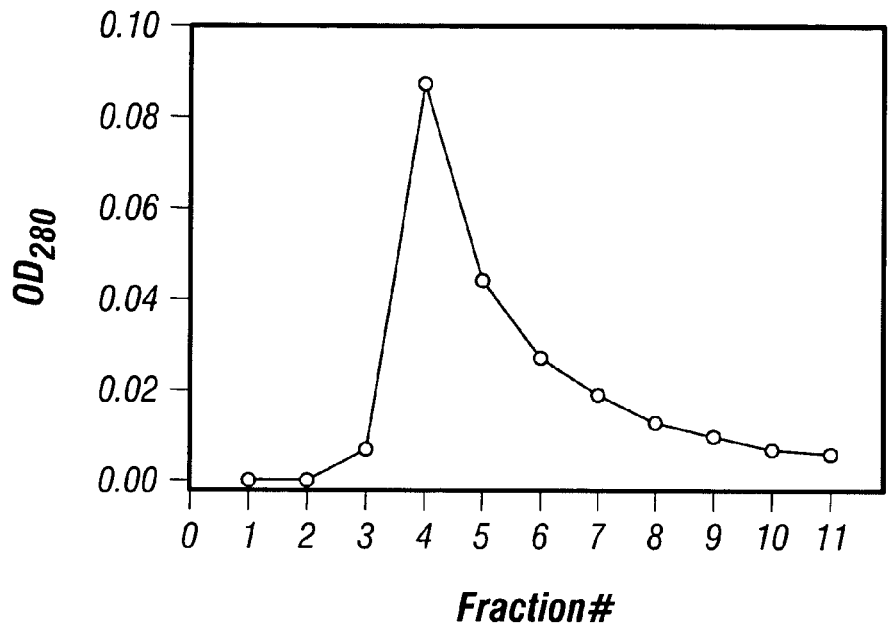
FIG. 4 illustrates the purification of E-coil-αhEGFR IgG conjugate by a protein-G column prepared according to one embodiment of the invention.
Figure 5:
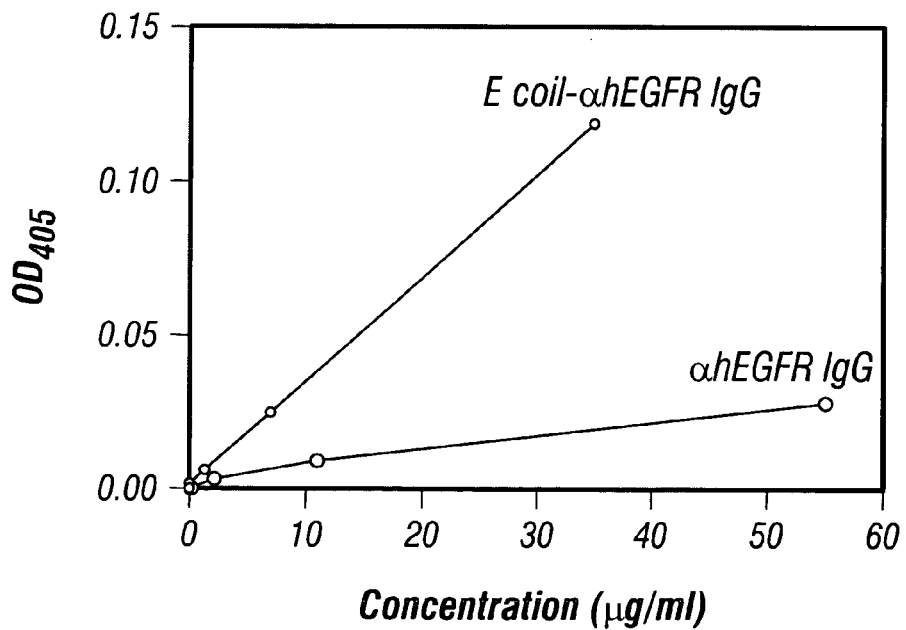
FIG. 5 shows the antibody titer of purified E-coil-αhEGFR IgG conjugate prepared according to one embodiment of the invention as determined by immobilized K-coil ELISA.

Conjugation was performed by the following steps:
a. Concentrate oxidized antibody (~2 mg in 4 ml) using Millipore Ultrafree Filter units (30k MWc/o).
b. Add 75 μl of the functionalized E-coil solution (4 μg/μl dd$H_2O$) to half of the oxidized antibody solution (containing ~0.75 mg of antibody in acetate buffer, pH 5.5).
c. Incubate at room temp. for 2 hr with shaking.
d. Purify the antibody mixture using a Protein G column (See FIG. 4).
e. Compare and analysis of sample (before and after affinity purification).

E. Example 5

Biacore Analysis of Coil Urease Conjugate and Coil Antibody Conjugate

Cysteine containing K-coil peptide or the E-coil peptide was covalent coupled to the Pioneer B1 biosensor chip according to the manufacturer suggested protocol. Briefly, the dextran surface of the sensor chip was first activated with NHS/EDC (15 ul) followed by addition of PDEA (20 ul). K-coil (or E-coil (50 μg/ml) in 10 mM sodium acetate buffer pH 4.3 was injected and allowed to react to give a surface density of approximately 200–400 RU. Remaining activated groups were then blocked by injection (10 ul) of a 50 mM cysteine, 1 M NaCl, 0.1 M formate, pH 4.3 deactivation solution.

Kinetic experiments were performed on a BIAcore3000 instrument at 25° C. Each biosensor run consisted of (1) a 600s sample injection phase (coil urease or coil antibody), (2) a 600s dissociation phase, and (3) a 2×15s regeneration phase (6M guanidine HCl). A flow rate of 5 ul/min was maintained throughout the cycle. PBS was used as a buffer. The SPR signal was recorded in real time with sampling at every 0.5 s and plotted as RU versus time (sensorgram). Each sensorgram obtained was corrected for bulk refractive index changes by subtracting the corresponding sample injection cycle on a blank cell surface

F. Example 6

Animal Studies

Athymic nu/nu female mice with human mammary gland adenocarcinoma xenografts were used for testing. Animals selected were generally 5 to 7 weeks of age, and their body weights at treatment commencement range from approximately 15 to 28 grams.

MCF-cells were used to generate the xenografts. The cells were grown in MEM media supplemented with Penicillin/Streptomycin 5000U/ml, L-glutamine 200 mM, Sodium pyruvate, nonessential amino acids, vitamins, and 10% FBS; The cell incubator was maintained with 5% CO2, 37.50C, and 80% humidity. The cells were harvested with 0.25%(w/v) trypsin-0.03%(w/v) EDTA solution. Approximately $1 \times 10^6$ cells in 100 uL was injected subcutaneously to the right flank of each mouse.

Tumor growth was allowed to proceed for about 6–8 days allowing the size of the tumor to reach at least 2–4 mm in diameter. Doses were administered via intratumor injection. The dose volume for each animal was 50 μL. Each solid tumor was injected with the given dose of test article in a "fanning fashion". Tumor volumes were taken by external caliper measurements. Body weights were taken at the start of the trial and at time of sacrifice.

Results, as shown in Table 3 below, show that tumors were not perceptible 24 hours following treatment.

TABLE 3

| | Successful Treatment of Tumors in Mice | | | | | |
|---|---|---|---|---|---|---|
| Mouse | 1 | 2 | 3 | 4 | 5 | 6 |
| MCF cell injected | $0.8 \times 10^6$ | $0.8 \times 10^6$ | $0.8 \times 10^6$ | $0.8 \times 10^6$ | $1.3 \times 10^6$ | $0.8 \times 10^6$ |

TABLE 3-continued

Successful Treatment of Tumors in Mice

| Mouse | 1 | 2 | 3 | 4 | 5 | 6 |
|---|---|---|---|---|---|---|
| Tumor size before treatment | 22.5 mm$^3$ | 33.5 mm$^3$ | 15.6 mm$^3$ | 31.1 mm$^3$ | 32.5 mm$^3$ | 8.2 mm$^3$ |
| Urease amount injected | 50 U/50 uL | 50 U/50 uL | 50 U/50 uL | 50 U/50 uL | 40 U/50 uL | 10 U/50 uL |
| Tumor size post injection (24 hours) | not perceptible | not perceptible | not perceptible | not perceptible | not perceptible | not perceptible |

Although the invention has been described with respect to particular embodiments, it will be apparent to those skilled in the art that various changes and modifications can be made without departing from the invention.

It is claimed:

1. A pharmaceutical composition for use in inhibiting growth of cancer cells in a mammalian subject, said composition comprising
a urease enzyme, and,
associated with said enzyme, a chemical entity effective to enhance the delivery of the enzyme to cancer cells, when the composition is administered to the subject.

2. The composition of claim 1, wherein said chemical entity includes a hydrophilic polymer (i) conjugated to the urease, (ii) selected from the group consisting of polyethylene glycol, polyvinylpyrrolidone, polyvinylmethylether, polyhydroxypropyl methacrylamide, polyhydroxypropyl methacrylate, polyhydroxyethyl acrylate, polymethacrylamide, polydimethylacrylamide, polymethyloxazoline, polyethyloxazoline, polyhydroxyethyloxazolione, polyhydroxypropyoxazoline, polyaspartamide, and hydrophilic cellulose derivatives, and (iii) present in an amount effective to extend the blood circulation time or reduce the antigenicity of said composition relative to native urease.

3. The composition of claim 2, wherein said hydrophilic polymer is polyethylene glycol having a molecular weight between about 1,000 and 10,000 daltons.

4. The composition of claim 1 or 2, wherein said chemical entity is a targeting moiety attached to said urease and selected from the group consisting of an anti-tumor antigen antibody, anti-hCG antibody, and a ligand capable of binding specifically to cancer-cell surface receptors.

5. The composition of claim 4, wherein said targeting moiety is a polypeptide, and said composition is a fusion protein of the targeting moiety and urease enzyme.

6. The composition of claim 4, wherein said urease includes, at its C- or N-terminus, a first coil-forming peptide characterized by a selected charge and an ability to interact with a second, oppositely charged coil-forming peptide to form a stable α-helical coiled-coil heterodimer; and said chemical entity includes a targeting moiety which includes said second coil-forming peptide.

7. The composition of claim 1, wherein said chemical entity includes vesicles having urease enzyme in entrapped form.

8. The composition of claim 7, wherein said vesicles are liposomes which are long-circulating by virtue of an exterior coating of polyethylene glycol chains, and sized to extravasate into tumor regions, when the composition is administered intravenously.

9. The composition of claim 7, wherein said vesicles are liposomes having surface bound targeting moieties selected from the group consisting of an anti-tumor antigen antibody, anti-hCG antibody, and ligands capable of binding specifically to cancer-cell surface receptors.

10. The composition of claim 1, wherein said chemical entity includes a urease inhibitor associated therewith, in an amount sufficient to inhibit the activity of said enzyme.

11. The composition of claim 1, wherein said urease is a plant or bacterial urease.

12. The composition of claim 1, further comprising an agent selected from the group consisting urea, a therapeutically active anti-tumor agent and an imaging agent.

13. The composition of claim 12, which further includes vesicles containing the urease and agent in entrapped form.

14. A method for inhibiting growth of cancer cells in a mammalian subject, comprising
exposing the cells to urease, in an amount of urease effective to inhibit growth of the cancer cells.

15. The method of claim 14, wherein the cancer cells comprise a solid tumor, and said exposing includes injecting the urease directly into the tumor of the subject.

16. The method of claim 15, wherein said exposing includes visualizing said tumor with an image-guidance tool selected from the group consisting of ultrasound, fluoroscopy, MRI, positron emission tomography.

17. The method of claim 15, which further includes, following said exposing, (i) interrogating the subject with a diagnostic tool capable of detecting changes in extracellular pH is a subject's tissue, (ii) identifying a tissue region within the subject that shows a selected elevation in extracellular pH following said administering, and (iii) based on said identifying, repeating said exposing until a selected change in extracellular pH within the entire solid tumor is achieved.

18. The method of claim 14 wherein the cancer cells comprise a solid tumor, and said exposing includes administering urease parenterally to the subject other than by direct injection.

19. The method of claim 15 or 18, wherein said urease is derivatized with a hydrophilic polymer (i) selected from the group consisting of polyethylene glycol, polyvinylpyrrolidone, polyvinylmethylether, polyhydroxypropyl methacrylamide, polyhydroxypropyl methacrylate, polyhydroxyethyl acrylate, polymethacrylamide, polydimethylacrylamide, polymethyloxazoline, polyethyloxazoline, polyhydroxyethyloxazolione, polyhydroxypropyoxazoline, polyaspartamide, and hydrophilic cellulose derivatives, and (ii) present in an amount effective to extend the blood circulation time or reduce the antigenicity of said composition relative to native urease.

20. The method of claim 19, wherein said hydrophilic polymer is polyethylene glycol having a molecular weight between about 1,000 and 10,000 daltons.

21. The method of claim 18, which further includes, following said exposing, (i) interrogating the subject with a diagnostic tool capable of detecting changes in extracellular pH is a subject's tissue, (ii) identifying a tissue region within the subject that shows a selected elevation in extracellular pH following said administering, and (iii) based on said identifying, repeating said exposing until a selected change in extracellular pH within the entire solid tumor is achieved.

22. The method of claim 14, wherein urease has attached thereto, a targeting moiety selected from the group consisting of an anti-tumor antigen antibody, anti-hCG antibody, and a ligand capable of binding specifically to cancer-cell surface receptors, and said exposing includes administering the urease composition parenterally to the subject.

23. The method of claim 22, wherein said urease includes, at its C- or N-terminus, a first coil-forming peptide characterized by a selected charge and an ability to interact with a second, oppositely charged coil-forming peptide to form a stable α-helical coiled-coil heterodimer; and said targeting moiety includes said second coil-forming peptide, and said exposing includes administering the urease composition parenterally to the subject.

24. The method of claim 14, wherein said urease is entrapped within vesicles, and said exposing includes administering the vesicles composition parenterally to the subject.

25. The method of claim 24, wherein said liposomes are long-circulating by virtue of an exterior coating of polyethylene glycol chains, and sized to extravasate into tumor regions, when the composition is administered parenterally, and said exposing includes administering the liposomes parenterally to the subject other than by direct injection.

26. The method of claim 14, wherein said urease is complexed with a urease inhibitor, and said exposing comprises administering to the subject, a complex of the urease and urease inhibitor.

27. The method of claim 14, which further includes, following said exposing, of modulating the activity of urease on cancer cells by administering to the subject, an amount of a urease inhibitor effective to reduce the activity of urease on said cancer cells.

28. The method of claim 14, wherein said exposing comprises administering to the subject
a first conjugate comprising a tumor targeting moiety and a first binding moiety having
an ability to interact with a second binding moiety; and
a second conjugate comprising the second binding moiety conjugated with urease.

29. The method of claim 28, wherein the first binding moiety comprises a first coil-forming peptide characterized by a selected charge and an ability to interact with a second, oppositely charged coil-forming peptide to form a stable α-helical coiled-coil heterodimer; and the second binding moiety comprises the second coil-forming peptide.

30. A method of assessing the presence, size or condition a solid
tumor in a subject, comprising
administering urease to the subject containing, or suspected of containing, a solid tumor, under conditions effective to localize the urease in a solid tumor in the subject, interrogating the subject with a diagnostic tool capable of detecting changes in extracellular pH is a subject's tissue, and identifying a tissue region within the subject that shows an elevation in extracellular pH following said administering.

31. The method of claim 30, wherein said interrogating includes administering to the subject a pH-sensitive diagnostic agent capable of localizing in a tumor, and interrogating the subject with a diagnostic tool effective to detect said agent.

32. The method of claim 30, wherein said interrogating includes performing an MRI scan on the subject.

33. The method of claim 30, wherein administering urease to the subject is employed in an anti-tumor therapy, and said identifying is used for detecting the localization of urease in a solid tumor.

34. The method of claim 33, wherein said identifying is used for monitoring the change in size and shape of the tumor in response to urease administration.

* * * * *

```
                        SEQUENCE LISTING

<160> NUMBER OF SEQ ID NOS: 7

<210> SEQ ID NO 1
<211> LENGTH: 35
<212> TYPE: PRT
<213> ORGANISM: Artificial Sequence
<220> FEATURE:
<223> OTHER INFORMATION: E-coil forming peptide

<400> SEQUENCE: 1

Glu Val Ser Ala Leu Glu Lys Glu Val Ser Ala Leu Glu Lys Glu Val
 1               5                  10                  15

Ser Ala Leu Glu Lys Glu Val Ser Ala Leu Glu Lys Glu Val Ser Ala
            20                  25                  30

Leu Glu Lys
        35

<210> SEQ ID NO 2
<211> LENGTH: 35
<212> TYPE: PRT
<213> ORGANISM: Artificial Sequence
<220> FEATURE:
<223> OTHER INFORMATION: K-coil forming peptide

<400> SEQUENCE: 2

Lys Val Ser Ala Leu Lys Glu Lys Val Ser Ala Leu Lys Glu Lys Val
 1               5                  10                  15

Ser Ala Leu Lys Glu Lys Val Ser Ala Leu Lys Glu Lys Val Ser Ala
            20                  25                  30

Leu Lys Glu
        35

<210> SEQ ID NO 3
<211> LENGTH: 35
<212> TYPE: PRT
<213> ORGANISM: Artificial Sequence
<220> FEATURE:
<223> OTHER INFORMATION: coil forming peptide

<400> SEQUENCE: 3

Glu Val Glu Ala Leu Gln Lys Glu Val Ser Ala Leu Glu Lys Glu Val
 1               5                  10                  15

Ser Ala Leu Glu Cys Glu Val Ser Ala Leu Glu Lys Glu Val Glu Ala
```

-continued

```
                    20                  25                  30

Leu Gln Lys
        35

<210> SEQ ID NO 4
<211> LENGTH: 35
<212> TYPE: PRT
<213> ORGANISM: Artificial Sequence
<220> FEATURE:
<223> OTHER INFORMATION: coil forming peptide

<400> SEQUENCE: 4

Lys Val Glu Ala Leu Lys Lys Val Ser Ala Leu Lys Glu Lys Val
  1               5                  10                  15

Ser Ala Leu Lys Cys Lys Val Ser Ala Leu Lys Glu Lys Val Glu Ala
                20                  25                  30

Leu Lys Lys
        35

<210> SEQ ID NO 5
<211> LENGTH: 7
<212> TYPE: PRT
<213> ORGANISM: Artificial Sequence
<220> FEATURE:
<223> OTHER INFORMATION: K-coil forming peptide

<400> SEQUENCE: 5

Lys Val Ser Ala Leu Lys Glu
          1               5

<210> SEQ ID NO 6
<211> LENGTH: 7
<212> TYPE: PRT
<213> ORGANISM: Artificial Sequence
<220> FEATURE:
<223> OTHER INFORMATION: E-coil forming peptide

<400> SEQUENCE: 6

Glu Val Ser Ala Leu Glu Lys
  1               5

<210> SEQ ID NO 7
<211> LENGTH: 840
<212> TYPE: PRT
<213> ORGANISM: Canavalia ensiformis

<400> SEQUENCE: 7

Met Lys Leu Ser Pro Arg Glu Val Glu Lys Leu Gly Leu His Asn Ala
  1               5                  10                  15

Gly Tyr Leu Ala Gln Lys Arg Leu Ala Arg Gly Val Arg Leu Asn Tyr
                20                  25                  30

Thr Glu Ala Val Ala Leu Ile Ala Ser Gln Ile Met Glu Tyr Ala Arg
            35                  40                  45

Asp Gly Glu Lys Thr Val Ala Gln Leu Met Cys Leu Gly Gln His Leu
        50                  55                  60

Leu Gly Arg Arg Gln Val Leu Pro Ala Val Pro His Leu Leu Asn Ala
 65                  70                  75                  80

Val Gln Val Glu Ala Thr Phe Pro Asp Gly Thr Lys Leu Val Thr Val
                85                  90                  95

His Asp Pro Ile Ser Arg Glu Asn Gly Glu Leu Gln Glu Ala Leu Phe
                100                 105                 110
```

```
Gly Ser Leu Leu Pro Val Pro Ser Leu Asp Lys Phe Ala Glu Thr Lys
            115                 120                 125

Glu Asp Asn Arg Ile Pro Gly Glu Ile Leu Cys Glu Asp Glu Cys Leu
130                 135                 140

Thr Leu Asn Ile Gly Arg Lys Ala Val Ile Leu Lys Val Thr Ser Lys
145                 150                 155                 160

Gly Asp Arg Pro Ile Gln Val Gly Ser His Tyr His Phe Ile Glu Val
                165                 170                 175

Asn Pro Tyr Leu Thr Phe Asp Arg Arg Lys Ala Tyr Gly Met Arg Leu
            180                 185                 190

Asn Ile Ala Ala Gly Thr Ala Val Arg Phe Glu Pro Gly Asp Cys Lys
        195                 200                 205

Ser Val Thr Leu Val Ser Ile Glu Gly Asn Lys Val Ile Arg Gly Gly
    210                 215                 220

Asn Ala Ile Ala Asp Gly Pro Val Asn Glu Thr Asn Leu Glu Ala Ala
225                 230                 235                 240

Met His Ala Val Arg Ser Lys Gly Phe Gly His Glu Glu Lys Asp
                245                 250                 255

Ala Ser Glu Gly Phe Thr Lys Glu Asp Pro Asn Cys Pro Phe Asn Thr
            260                 265                 270

Phe Ile His Arg Lys Glu Tyr Ala Asn Lys Tyr Gly Pro Thr Thr Gly
        275                 280                 285

Asp Lys Ile Arg Leu Gly Asp Thr Asn Leu Leu Ala Glu Ile Glu Lys
    290                 295                 300

Asp Tyr Ala Leu Tyr Gly Asp Glu Cys Val Phe Gly Gly Gly Lys Val
305                 310                 315                 320

Ile Arg Asp Gly Met Gly Gln Ser Cys Gly His Pro Pro Ala Ile Ser
                325                 330                 335

Leu Asp Thr Val Ile Thr Asn Ala Val Ile Asp Tyr Thr Gly Ile
            340                 345                 350

Ile Lys Ala Asp Ile Gly Ile Lys Asp Gly Leu Ile Ala Ser Ile Gly
        355                 360                 365

Lys Ala Gly Asn Pro Asp Ile Met Asn Gly Val Phe Ser Asn Met Ile
    370                 375                 380

Ile Gly Ala Asn Thr Glu Val Ile Ala Gly Glu Gly Leu Ile Val Thr
385                 390                 395                 400

Ala Gly Ala Ile Asp Cys His Val His Tyr Ile Cys Pro Gln Leu Val
                405                 410                 415

Tyr Glu Ala Ile Ser Ser Gly Ile Thr Thr Leu Val Gly Gly Gly Thr
            420                 425                 430

Gly Pro Ala Ala Gly Thr Arg Ala Thr Thr Cys Thr Pro Ser Pro Thr
        435                 440                 445

Gln Met Arg Leu Met Leu Gln Ser Thr Asp Leu Pro Leu Asn Phe
    450                 455                 460

Gly Phe Thr Gly Lys Gly Ser Ser Lys Pro Asp Glu Leu His Glu
465                 470                 475                 480

Ile Ile Lys Ala Gly Ala Met Gly Leu Lys Leu His Glu Asp Trp Gly
                485                 490                 495

Ser Thr Pro Ala Ala Ile Asp Asn Cys Leu Thr Ile Ala Glu His His
            500                 505                 510

Asp Ile Gln Ile Asn Ile His Thr Asp Thr Leu Asn Glu Ala Gly Phe
        515                 520                 525

Val Glu His Ser Ile Ala Ala Phe Lys Gly Arg Thr Ile His Thr Tyr
```

-continued

```
              530                 535                 540
His Ser Glu Gly Ala Gly Gly His Ala Pro Asp Ile Ile Lys Val
545                     550                 555                 560

Cys Gly Ile Lys Asn Val Leu Pro Ser Ser Thr Asn Pro Thr Arg Pro
                    565                 570                 575

Leu Thr Ser Asn Thr Ile Asp Glu His Leu Asp Met Leu Met Val Cys
                580                 585                 590

His His Leu Asp Arg Glu Ile Pro Glu Asp Leu Ala Phe Ala His Ser
            595                 600                 605

Arg Ile Arg Lys Lys Thr Ile Ala Ala Glu Asp Val Leu Asn Asp Ile
610                     615                 620

Gly Ala Ile Ser Ile Ile Ser Ser Asp Ser Gln Ala Met Gly Arg Val
625                 630                 635                 640

Gly Glu Val Ile Ser Arg Thr Trp Gln Thr Ala Asp Lys Met Lys Ala
                645                 650                 655

Gln Thr Gly Pro Leu Lys Cys Asp Ser Ser Asp Asn Asp Asn Phe Arg
                660                 665                 670

Ile Arg Arg Tyr Ile Ala Lys Tyr Thr Ile Asn Pro Ala Ile Ala Asn
                675                 680                 685

Gly Phe Ser Gln Tyr Val Gly Ser Val Glu Val Gly Lys Leu Ala Asp
            690                 695                 700

Leu Val Met Trp Lys Pro Ser Phe Phe Gly Thr Lys Pro Glu Met Val
705                     710                 715                 720

Ile Lys Gly Gly Met Val Ala Trp Ala Asp Ile Gly Asp Pro Asn Ala
                    725                 730                 735

Ser Ile Pro Thr Pro Glu Pro Val Lys Met Arg Pro Met Tyr Gly Thr
                740                 745                 750

Leu Gly Lys Ala Gly Gly Ala Leu Ser Ile Ala Phe Val Ser Lys Ala
                755                 760                 765

Ala Leu Asp Gln Arg Val Asn Val Leu Tyr Gly Leu Asn Lys Arg Val
770                 775                 780

Glu Ala Val Ser Asn Val Arg Lys Leu Thr Lys Leu Asp Met Lys Leu
785                 790                 795                 800

Asn Asp Ala Leu Pro Glu Ile Thr Val Asp Pro Glu Ser Tyr Thr Val
                805                 810                 815

Lys Ala Asp Gly Lys Leu Leu Cys Val Ser Glu Ala Thr Thr Val Pro
                820                 825                 830

Leu Ser Arg Asn Tyr Phe Leu Phe
                835                 840
```